United States Patent
Greenshields et al.

(12)

(10) Patent No.: US 11,259,526 B2
(45) Date of Patent: *Mar. 1, 2022

(54) PHOSPHATE-SOLUBILZING FUNGAL STRAINS

(71) Applicant: NOVOZYMES BIOAG A/S, Bagsvaerd (DK)

(72) Inventors: Dave Greenshields, Saskatchewan (CA); Caressa Caldwell, Saskatchewan (CA); Shelagh Steckler, Saskatchewan (CA); Kari Priest, Saskatchewan (CA); Michael Frodyma, Salem, VA (US)

(73) Assignee: NOVOZYMES BIOAG A/S, Bagsvaerd (DK)

( * ) Notice: Subject to any disclaimer, the term of this patent is extended or adjusted under 35 U.S.C. 154(b) by 133 days.

This patent is subject to a terminal disclaimer.

(21) Appl. No.: 16/073,050

(22) PCT Filed: Jan. 13, 2017

(86) PCT No.: PCT/US2017/013416
§ 371 (c)(1),
(2) Date: Jul. 26, 2018

(87) PCT Pub. No.: WO2017/131971
PCT Pub. Date: Aug. 3, 2017

(65) Prior Publication Data
US 2019/0029267 A1  Jan. 31, 2019

Related U.S. Application Data

(60) Provisional application No. 62/287,965, filed on Jan. 28, 2016.

(51) Int. Cl.
| | | |
|---|---|---|
| *A01N 63/36* | (2020.01) | |
| *C05F 11/08* | (2006.01) | |
| *C12N 1/14* | (2006.01) | |
| *C12R 1/80* | (2006.01) | |
| *A01C 1/06* | (2006.01) | |

(52) U.S. Cl.
CPC .............. *A01N 63/36* (2020.01); *C05F 11/08* (2013.01); *C12N 1/14* (2013.01); *C12N 1/145* (2021.05); *A01C 1/06* (2013.01); *C12R 2001/80* (2021.05)

(58) Field of Classification Search
CPC .. C12R 1/80; A01C 1/06; A01N 63/04; C05F 11/08; C12N 1/14
USPC ........................................................ 504/117
See application file for complete search history.

(56) References Cited

U.S. PATENT DOCUMENTS

| | | |
|---|---|---|
| 5,026,417 A | 6/1991 | Kucey |
| 5,484,464 A | 1/1996 | Gleddie |
| 7,241,588 B2 | 7/2007 | Chen |
| 8,278,247 B2 | 10/2012 | Hnatowich |
| 9,101,088 B2 | 8/2015 | Hnaowich |
| 2008/0107689 A1* | 5/2008 | Seiskari .................. C12N 1/04 424/234.1 |
| 2014/0014909 A1 | 1/2014 | Lee |
| 2014/0143909 A1* | 5/2014 | Greenshields ........... A01H 3/00 800/298 |

FOREIGN PATENT DOCUMENTS

WO    2014/078647 A1    5/2014

OTHER PUBLICATIONS

Leggett et al, 2004, Research Drive Saskatoon 1-9.
Leggett et al, 2007, Springer Netherlands 102, 215-222.

* cited by examiner

*Primary Examiner* — Johann R Richter
*Assistant Examiner* — Courtney A Brown
(74) *Attorney, Agent, or Firm* — Adam Rucker

(57) ABSTRACT

The present disclosure provides novel fungal strains capable of solubilizing phosphate, as well as compositions and methods of using those strains to increase the amount/concentration of soluble phosphate in a medium that comprises insoluble phosphate.

20 Claims, No Drawings

PHOSPHATE-SOLUBILZING FUNGAL STRAINS

CROSS-REFERENCE TO RELATED APPLICATIONS

This application is a 35 U.S.C. 371 national application of international application no. PCT/US2017/013416 filed Jan. 13, 2017, which claims priority or the benefit under 35 U.S.C. 119 of U.S. provisional application No. 62/287,965 filed Jan. 28, 2016, the contents of which are fully incorporated herein by reference.

REFERENCE TO A DEPOSIT OF BIOLOGICAL MATERIAL

The present disclosure contains references to biological material deposited under the terms of the Budapest Treaty on the International Recognition of the Deposit of Microorganisms for the Purposes of Patent Procedure at the Agricultural Research Service Culture Collection, 1815 North University Street, Peoria, Ill. 61604, U.S.A.

FIELD OF THE INVENTION

The present disclosure relates to isolated fungal strains and new fungal strains derived therefrom.

BACKGROUND

Certain strains of *Penicillium* are capable of solubilizing phosphate. See, e.g., U.S. Pat. Nos. 5,026,417; 5,484,464; 7,241,588; 8,278,247 and 9,101,088; U.S. Patent Publication Nos. 2014/014909.

Efforts to isolate and/or create new and improved phosphate-solubilizing *Penicillium* strains are ongoing.

SUMMARY

A first aspect of the present disclosure is an isolated strain of *Penicillium bilaiae* selected from the group consisting of the isolated *Penicillium bilaiae* strain having the deposit accession number NRRL 67154 (*P. bilaiae* NRRL 67154), the isolated *Penicillium bilaiae* strain having the deposit accession number NRRL 67155 (*P. bilaiae* NRRL 67155), the isolated *Penicillium bilaiae* strain having the deposit accession number NRRL 67156 (*P. bilaiae* NRRL 67156), the isolated *Penicillium bilaiae* strain having the deposit accession number NRRL 67157 (*P. bilaiae* NRRL 67157), the isolated *Penicillium bilaiae* strain having the deposit accession number NRRL 67158 (*P. bilaiae* NRRL 67158), or the isolated *Penicillium bilaiae* strain having the deposit accession number NRRL 67159 (*P. bilaiae* NRRL 67159).

A second aspect of the present disclosure is a biologically pure culture of *P. bilaiae* NRRL B-67154, *P. bilaiae* NRRL B-67155, *P. bilaiae* NRRL B-67156, *P. bilaiae* NRRL B-67157, *P. bilaiae* NRRL B-67158, or *P. bilaiae* NRRL B-67159.

A third aspect of the present disclosure is an inoculant composition comprising *P. bilaiae* NRRL B-67154, *P. bilaiae* NRRL B-67155, *P. bilaiae* NRRL B-67156, *P. bilaiae* NRRL B-67157, *P. bilaiae* NRRL B-67158, and/or *P. bilaiae* NRRL B-67159. In some embodiments, the inoculant composition comprises one or more stabilizing compounds, one or more pesticides, one or more lipo-chitooligosaccharides, one or more chitooligosaccharides, one or more chitinous compounds, one or more flavonoids, and/or one or more additional microorganisms.

A fourth aspect of the present disclosure is a kit comprising an inoculant composition comprising *P. bilaiae* NRRL B-67154, *P. bilaiae* NRRL B-67155, *P. bilaiae* NRRL B-67156, *P. bilaiae* NRRL B-67157, *P. bilaiae* NRRL B-67158, and/or *P. bilaiae* NRRL B-67159 and a container housing said inoculant composition.

A fifth aspect of the present disclosure is a method of increasing the amount/concentration of soluble phosphate in a medium that contains insoluble phosphate, said method comprising applying *P. bilaiae* NRRL B-67154, *P. bilaiae* NRRL B-67155, *P. bilaiae* NRRL B-67156, *P. bilaiae* NRRL B-67157, *P. bilaiae* NRRL B-67158, and/or *P. bilaiae* NRRL B-67159 to said medium in an amount/concentration effective to solubilize at least a portion of the insoluble phosphate therein.

A sixth aspect of the present disclosure is a method of increasing the amount/concentration of soluble phosphate in a medium that contains insoluble phosphate, said method comprising introducing *P. bilaiae* NRRL B-67154, *P. bilaiae* NRRL B-67155, *P. bilaiae* NRRL B-67156, *P. bilaiae* NRRL B-67157, *P. bilaiae* NRRL B-67158, and/or *P. bilaiae* NRRL B-67159 into said medium in an amount/concentration effective to solubilize at least a portion of the insoluble phosphate therein.

An eighth aspect of the present disclosure is a method of increasing the amount/concentration of soluble phosphate in a medium that contains insoluble phosphate, said method comprising applying a biologically pure culture of *P. bilaiae* NRRL B-67154, *P. bilaiae* NRRL B-67155, *P. bilaiae* NRRL B-67156, *P. bilaiae* NRRL B-67157, *P. bilaiae* NRRL B-67158, or *P. bilaiae* NRRL B-67159 to said medium in an amount/concentration effective to solubilize at least a portion of the insoluble phosphate therein.

A ninth aspect of the present disclosure is a method of increasing the amount/concentration of soluble phosphate in a medium that contains insoluble phosphate, said method comprising introducing the biologically pure culture of *P. bilaiae* NRRL B-67154, *P. bilaiae* NRRL B-67155, *P. bilaiae* NRRL B-67156, *P. bilaiae* NRRL B-67157, *P. bilaiae* NRRL B-67158, or *P. bilaiae* NRRL B-67159 into said medium in an amount/concentration effective to solubilize at least a portion of the insoluble phosphate therein.

A tenth aspect of the present disclosure is a method of increasing the amount/concentration of soluble phosphate in a medium that contains insoluble phosphate, said method comprising applying an inoculant composition comprising *P. bilaiae* NRRL B-67154, *P. bilaiae* NRRL B-67155, *P. bilaiae* NRRL B-67156, *P. bilaiae* NRRL B-67157, *P. bilaiae* NRRL B-67158, and/or *P. bilaiae* NRRL B-67159 to said medium in an amount/concentration effective to solubilize at least a portion of the insoluble phosphate therein.

An eleventh aspect of the present disclosure is a method of increasing the amount/concentration of soluble phosphate in a medium that contains insoluble phosphate, said method comprising introducing an inoculant composition comprising *P. bilaiae* NRRL B-67154, *P. bilaiae* NRRL B-67155, *P. bilaiae* NRRL B-67156, *P. bilaiae* NRRL B-67157, *P. bilaiae* NRRL B-67158, and/or *P. bilaiae* NRRL B-67159 into said medium in an amount/concentration effective to solubilize at least a portion of the insoluble phosphate therein.

DETAILED DESCRIPTION

This description is not intended to be a detailed catalog of all the different ways in which the invention may be implemented or of all the features that may be added to the instant invention. For example, features illustrated with respect to one embodiment may be incorporated into other embodiments and features illustrated with respect to a particular embodiment may be deleted from that embodiment. In addition, numerous variations and additions to the various embodiments suggested herein, which do not depart from the instant invention, will be apparent to those skilled in the art in light of the instant disclosure. Hence, the following description is intended to illustrate some particular embodiments of the invention and not to exhaustively specify all permutations, combinations and variations thereof.

The terminology used herein is for the purpose of describing particular embodiments only and is not intended to be limiting of the invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. For the sake of brevity and/or clarity, well-known functions or constructions may not be described in detail.

As used herein, the singular forms "a," "an," and "the" are intended to include the plural forms as well, unless the context clearly indicates otherwise.

As used herein, the terms "acaricide" and "acaricidal" refer to an agent or combination of agents the application of which is toxic to an acarid (i.e., kills an acarid, inhibits the growth of an acarid and/or inhibits the reproduction of an acarid).

As used herein, the term "and/or" is intended to include any and all combinations of one or more of the associated listed items, as well as the lack of combinations when interpreted in the alternative ("or").

As used herein, the term "aqueous" refers to a composition that contains more than a trace amount of water (i.e., more than 0.5% water by weight, based upon the total weight of the composition).

As used herein, the term "biologically pure culture" refers to a microbial culture that is free or essentially free of biological contamination and that has genetic uniformity such that different subcultures taken therefrom will exhibit identical or substantially identical genotypes and phenotypes. In some embodiments, the biologically pure culture is 100% pure (i.e., all subcultures taken therefrom exhibit identical genotypes and phenotypes). In some embodiments, the biologically pure culture is at least 90, 91, 92, 93, 94, 95, 96, 97, 98, 99, 99.5, 99.6, 99.7, 99.8, or 99.9% pure (i.e., at least 90, 91, 92, 93, 94, 95, 96, 97, 98, 99, 99.5, 99.6, 99.7, 99.8, or 99.9% of the subcultures taken therefrom exhibit identical genotypes and phenotypes).

As used herein, the term "BRADY" is to be interpreted as a shorthand substitute for the phrase "*Bradyrhizobium elkanii* SEMIA 501, *Bradyrhizobium elkanii* SEMIA 587, *Bradyrhizobium elkanii* SEMIA 5019, *Bradyrhizobium japonicum* NRRL B-50586 (also deposited as NRRL B-59565), *Bradyrhizobium japonicum* NRRL B-50587 (also deposited as NRRL B-59566), *Bradyrhizobium japonicum* NRRL B-50588 (also deposited as NRRL B-59567), *Bradyrhizobium japonicum* NRRL B-50589 (also deposited as NRRL B-59568), *Bradyrhizobium japonicum* NRRL B-50590 (also deposited as NRRL B-59569), *Bradyrhizobium japonicum* NRRL B-50591 (also deposited as NRRL B-59570), *Bradyrhizobium japonicum* NRRL B-50592 (also deposited as NRRL B-59571), *Bradyrhizobium japonicum* NRRL B-50593 (also deposited as NRRL B-59572), *Bradyrhizobium japonicum* NRRL B-50594 (also deposited as NRRL B-50493), *Bradyrhizobium japonicum* NRRL B-50608, *Bradyrhizobium japonicum* NRRL B-50609, *Bradyrhizobium japonicum* NRRL B-50610, *Bradyrhizobium japonicum* NRRL B-50611, *Bradyrhizobium japonicum* NRRL B-50612, *Bradyrhizobium japonicum* NRRL B-50726, *Bradyrhizobium japonicum* NRRL B-50727, *Bradyrhizobium japonicum* NRRL B-50728, *Bradyrhizobium japonicum* NRRL B-50729, *Bradyrhizobium japonicum* NRRL B-50730, *Bradyrhizobium japonicum* SEMIA 566, *Bradyrhizobium japonicum* SEMIA 5079, *Bradyrhizobium japonicum* SEMIA 5080, *Bradyrhizobium japonicum* USDA 6, *Bradyrhizobium japonicum* USDA 110, *Bradyrhizobium japonicum* USDA 122, *Bradyrhizobium japonicum* USDA 123, *Bradyrhizobium japonicum* USDA 127, *Bradyrhizobium japonicum* USDA 129 and/or *Bradyrhizobium japonicum* USDA 532C."

As used herein, the terms "colony forming unit" and "cfu" refer to a microbial cell/spore capable of propagating on or in a suitable growth medium or substrate when conditions (e.g., temperature, moisture, nutrient availability, pH, etc.) are favorable for germination and/or microbial growth.

As used herein, the term "consists essentially of,", when used in reference to inoculant compositions and methods of the present disclosure, means that the compositions/methods may contain additional components/steps so long as the additional components/steps do not materially alter the composition/method. The term "materially alter," as applied to a composition/method of the present disclosure, refers to an increase or decrease in the effectiveness of the composition/method of at least 20%. For example, a component added to an inoculant composition of the present disclosure may be deemed to "materially alter" the composition if it increases or decreases the composition's ability to solubilize phosphate by at least 20%.

As used herein, the term "diazotroph" refers to an organism capable of converting atmospheric nitrogen ($N_2$) into a form that may be utilized by a plant or plant part (e.g., ammonia ($NH_3$), ammonium ($NH_4+$), etc.).

As used herein, the term "dispersant" refers to an agent or combination of agents the application of which reduces the cohesiveness of like particles, the surface tension of a liquid, the interfacial tension between two liquids and/or the interfacial tension between or a liquid and a solid.

As used herein, the terms "effective amount," "effective concentration" and "effective amount/concentration" refer to an amount or concentration that is sufficient to cause a desired effect (e.g. enhanced phosphate availability). The absolute value of the amount/concentration that is sufficient to cause the desired effect may be affected by factors such as the type and magnitude of effect desired, the type, size and volume of material to which the inoculant composition will be applied, the type(s) of microorganisms in the composition, the number of microorganisms in the composition, the stability of the microorganism(s) in the inoculant composition and the storage conditions (e.g., temperature, relative humidity, duration). Those skilled in the art will understand how to select an effective amount/concentration using routine dose-response experiments.

As used herein, the term "enhanced dispersion" refers to an improvement in one or more characteristics of microbial dispersion as compared to one or more controls (e.g., a control composition that is identical to an inoculant composition of the present disclosure except that it lacks one or more of the components found in the inoculant composition of the present disclosure). Exemplary microbial dispersion characteristics include, but are not limited to, the percentage of microbes that exist as single cells/spores when the inoculant composition is diluted in water. An inoculant composition that improves one or more microbial dispersion characteristics of the microorganism(s) contained therein as compared to a control composition (e.g., a control composition that is identical to the inoculant composition except that it lacks one or more of the components found in the inoculant composition) provides enhanced dispersion and can be referred to as a "readily dispersable inoculant composition."

As used herein, the terms "enhanced stability" and "enhanced microbial stability" refer to an improvement in one or more characteristics of microbial stability as compared to one or more controls (e.g., a control composition that is identical to an inoculant composition of the present disclosure except that it lacks one or more of the components found in the inoculant composition of the present disclosure). Exemplary microbial stability characteristics include, but are not limited to, the ability to germinate and/or propagate after being stored for a defined period of time and the ability to cause a desired effect (e.g., increased phosphate solubility) after being stored for a defined period of time. A microorganism that exhibits improvement in one or more microbial stability characteristics as compared to a control microorganism when each is subjected to the same conditions (e.g., storage conditions) displays enhanced stability and can be referred to as a "stable microorganism." An inoculant composition that improves one or more microbial stability characteristics of the microorganism(s) contained therein as compared to a control composition (e.g., a control composition that is identical to the inoculant composition except that it lacks one or more of the components found in the inoculant composition) provides enhanced stability and can be referred to as a "stable inoculant composition."

As used herein, the terms "enhanced survival" and "enhanced microbial survival" refer to an improvement in the survival rate of one or more microorganisms in an inoculant composition as compared to one or more microorganisms in a control composition (e.g., a control composition that is identical to an inoculant composition of the present disclosure except that it lacks one or more of the components found in the inoculant composition of the present disclosure). An inoculant composition that improves the survival rate of one or more of the microorganisms contained therein as compared to a control composition (e.g., a control composition that is identical to the inoculant composition except that it lacks one or more of the components found in the inoculant composition) provides enhanced survival and can be referred to as a stable inoculant composition.

As used herein, the terms "fungicide" and "fungicidal" refer to an agent or combination of agents the application of which is toxic to a fungus (i.e., kills a fungus, inhibits the growth of a fungus and/or inhibits the reproduction of a fungus).

As used herein, the term "fulvic acid" encompasses pure fulvic acids and fulvic acid salts (fulvates). Non-limiting examples of fulvic acids include ammonium fulvate, boron fulvate, potassium fulvate, sodium fulvate, etc. In some embodiments, the fulvic acid comprises, consists essentially of or consists MDL Number MFCD09838488 (CAS Number 479-66-3).

As used herein, the terms "herbicide" and "herbicidal" refer to an agent or combination of agents the application of which is toxic to a weed (i.e., kills a weed, inhibits the growth of a weed and/or inhibits the reproduction of a weed).

As used herein, the term "humic acid" encompasses pure humic acids and humic acid salts (humates). Non-limiting examples of humic acids include ammonium humate, boron humate, potassium humate, sodium humate, etc. In some embodiments, the humic acid comprises, consists essentially of or consists of one or more of MDL Number MFCD00147177 (CAS Number 1415-93-6), MDL Number MFCD00135560 (CAS Number 68131-04-4), MDL Number MFCS22495372 (CAS Number 68514-28-3), CAS Number 93924-35-7 and CAS Number 308067-45-0.

As used herein, the terms "inoculant composition" and "inoculum" refer to a composition comprising microbial cells and/or spores, said cells/spores being capable of propagating/germinating on or in a suitable growth medium or substrate when conditions (e.g., temperature, moisture, nutrient availability, pH, etc.) are favorable for germination and/or microbial growth.

As used herein, the terms "insecticide" and "insecticidal" refer to an agent or combination of agents the application of which is toxic to an insect (i.e., kills an insect, inhibits the growth of an insect and/or inhibits the reproduction of an insect).

As used herein, the term "isolated microbial strain" refers to a microbe that has been removed from the environment in which it is normally found.

As used herein, the term "isomer" includes all stereoisomers of the compounds and/or molecules to which it refers, including enantiomers and diastereomers, as well as all conformers, roatmers and tautomers, unless otherwise indicated. Compounds and/or molecules disclosed herein include all enantiomers in either substantially pure levorotatory or dextrorotatory form, or in a racemic mixture, or in any ratio of enantiomers. Where embodiments disclose a (D)-enantiomer, that embodiment also includes the (L)-enantiomer; where embodiments disclose a (L)-enantiomer, that embodiment also includes the (D)-enantiomer. Where embodiments disclose a (+)-enantiomer, that embodiment also includes the (−)-enantiomer; where embodiments disclose a (−)-enantiomer, that embodiment also includes the (+)-enantiomer. Where embodiments disclose a (S)-enantiomer, that embodiment also includes the (R)-enantiomer; where embodiments disclose a (R)-enantiomer, that embodiment also includes the (S)-enantiomer. Embodiments are intended to include any diastereomers of the compounds and/or molecules referred to herein in diastereomerically pure form and in the form of mixtures in all ratios. Unless stereochemistry is explicitly indicated in a chemical structure or chemical name, the chemical structure or chemical name is intended to embrace all possible stereoisomers, conformers, rotamers and tautomers of compounds and/or molecules depicted.

As used herein, the term "modified microbial strain" refers to a microbial strain that is modified from a strain isolated from nature. Modified microbial strains may be produced by any suitable method(s), including, but not limited to, chemical or other form of induced mutation to a polynucleotide within any genome within the strain; the insertion or deletion of one or more nucleotides within any genome within the strain, or combinations thereof; an inversion of at least one segment of DNA within any genome within the strain; a rearrangement of any genome within the strain; generalized or specific transduction of homozygous or heterozygous polynucleotide segments into any genome within the strain; introduction of one or more phage into any genome of the strain; transformation of any strain resulting in the introduction into the strain of stably replicating autonomous extrachromosomal DNA; any change to any genome or to the total DNA composition within the strain isolated from nature as a result of conjugation with any different microbial strain; and any combination of the foregoing. The term modified microbial strains includes a strain with (a) one of more heterologous nucleotide sequences, (b) one or more non-naturally occurring copies of a nucleotide sequence isolated from nature (i.e., additional copies of a gene that naturally occurs in the microbial strain from which the modified microbial strain was derived), (c) a lack of one or more nucleotide sequences that would otherwise be present in the natural reference strain by for example deleting nucleotide sequence, and (d) added extrachromosomal DNA. In some embodiments, modified microbial strains comprise a combination of two or more nucleotide sequences (e.g., two or more naturally occurring genes that do not naturally occur in the same microbial strain) or comprise a nucleotide sequence isolated from nature at a locus that is different from the natural locus.

As used herein, the terms "nematicide" and "nematicidal" refer to an agent or combination of agents the application of which is toxic to a nematode (i.e., kills a nematode, inhibits the growth of a nematode and/or inhibits the reproduction of a nematode).

As used herein, the term "nitrogen fixing organism" refers to an organism capable of converting atmospheric nitrogen ($N_2$) into a form that may be utilized by a plant or plant part (e.g., ammonia ($NH_3$), ammonium ($NH_4+$), etc.).

As used herein, the term "non-aqueous" refers to a composition that comprises no more than a trace amount of water (i.e., no more than 0.5% water by weight, based upon the total weight of the composition).

As used herein, the term "PENI" is to be interpreted as a shorthand substitute for the phrase "*Penicillium bilaiae* ATCC 18309, *Penicillium bilaiae* ATCC 20851, *Penicillium bilaiae* ATCC 22348, *Penicillium bilaiae* NRRL 50162, *Penicillium bilaiae* NRRL 50169, *Penicillium bilaiae* NRRL 50776, *Penicillium bilaiae* NRRL 50777, *Penicillium bilaiae* NRRL 50778, *Penicillium bilaiae* NRRL 50777, *Penicillium bilaiae* NRRL 50778, *Penicillium bilaiae* NRRL 50779, *Penicillium bilaiae* NRRL 50780, *Penicillium bilaiae* NRRL 50781, *Penicillium bilaiae* NRRL 50782, *Penicillium bilaiae* NRRL 50783, *Penicillium bilaiae* NRRL 50784, *Penicillium bilaiae* NRRL 50785, *Penicillium bilaiae* NRRL 50786, *Penicillium bilaiae* NRRL 50787, *Penicillium bilaiae* NRRL 50788, *Penicillium bilaiae* RS7B-SD1, *Penicillium brevicompactum* AgRF18, *Penicillium canescens* ATCC 10419, *Penicillium expansum* ATCC 24692, *Penicillium expansum* YT02, *Penicillium fellatanum* ATCC 48694, *Penicillium gaestrivorus* NRRL 50170, *Penicillium glabrum* DAOM 239074, *Penicillium glabrum* CBS 229.28, *Penicillium janthinellum* ATCC 10455, *Penicillium lanosocoeruleum* ATCC 48919, *Penicillium radicum* ATCC 201836, *Penicillium radicum* FRR 4717, *Penicillium radicum* FRR 4719, *Penicillium radicum* N93/47267 and/or *Penicillium raistrickii* ATCC 10490."

As used herein, the term "*Penicillium bilaiae*" is intended to include all iterations of the species name, such as "*Penicillium bilaji*" and "*Penicillium bilaii.*"

As used herein, the terms "percent identity," "% identity" and "percent identical" refer to the relatedness of two or more nucleotide or amino acid sequences, which may be calculated by (i) comparing two optimally aligned sequences over a window of comparison, (ii) determining the number of positions at which the identical nucleic acid base (for nucleotide sequences) or amino acid residue (for proteins) occurs in both sequences to yield the number of matched positions, (iii) dividing the number of matched positions by the total number of positions in the window of comparison, and then (iv) multiplying this quotient by 100% to yield the percent identity. If the "percent identity" is being calculated in relation to a reference sequence without a particular comparison window being specified, then the percent identity is determined by dividing the number of matched positions over the region of alignment by the total length of the reference sequence. Accordingly, for purposes of the present invention, when two sequences (query and subject) are optimally aligned (with allowance for gaps in their alignment), the "percent identity" for the query sequence is equal to the number of identical positions between the two sequences divided by the total number of positions in the query sequence over its length (or a comparison window), which is then multiplied by 100%.

As used herein, the terms "pesticide" and "pesticidal" refer to agents or combinations of agents the application of which is toxic to a pest (i.e., kills a pest, inhibits the growth of a pest and/or inhibits the reproduction of a pest). Non-limiting examples of pesticides include acaricides, fungicides, herbicides, insecticides, nematicides, rodenticides, virucides, gastropodicides, etc.

As used herein, the term "phosphate-solubilizing microorganism" refers to a microorganism capable of converting insoluble phosphate into a soluble form of phosphate.

As used herein, the term "progeny" refers to the descendent(s) of *P. bilaiae* NRRL B-67154, *P. bilaiae* NRRL B-67155, *P. bilaiae* NRRL B-67156, *P. bilaiae* NRRL B-67157, *P. bilaiae* NRRL B-67158, and/or *P. bilaiae* NRRL B-67159 and encompasses both immediate offspring of *P. bilaiae* NRRL B-67154, *P. bilaiae* NRRL B-67155, *P. bilaiae* NRRL B-67156, *P. bilaiae* NRRL B-67157, *P. bilaiae* NRRL B-67158, and/or *P. bilaiae* NRRL B-67159 and any descendants thereof.

As used herein, the terms "spore" and "microbial spore" refer to a microorganism in its dormant, protected state.

As used herein, the term "stabilizing compound" refers to an agent or combination of agents the application of which enhances the stability and/or survival of one or more microorganisms in an inoculant composition.

As used herein with respect to inoculant compositions, the term "stable" refers to an inoculant composition in which microorganisms exhibit enhanced stability and/or enhanced survival. In general, an inoculant composition may be labeled "stable" if it improves the survival rate and/or at least one microbial stability characteristic of at least one microorganism contained therein.

As used herein with respect to microbial strains, the term "survival rate" refers to the percentage of microbial cell/spore that are viable (i.e., capable of propagating on or in a suitable growth medium or substrate when conditions (e.g., temperature, moisture, nutrient availability, pH, etc.) are favorable for germination and/or microbial growth) at a given period of time.

While certain aspects of the present disclosure will hereinafter be described with reference to embodiments thereof, it will be understood by those of ordinary skill in the art that various changes in form and details may be made therein without departing from the spirit and scope of the present disclosure as defined by the claims.

All publications, patent applications, patents and other references mentioned herein are incorporated by reference in their entirety, except insofar as they contradict any disclosure expressly set forth herein.

The present disclosure provides isolated fungal strains capable of converting insoluble phosphate into a soluble form of phosphate.

In some embodiments, the isolated fungal strain is *P. bilaiae* NRRL 67154, *P. bilaiae* NRRL 67155, *P. bilaiae* NRRL 67156, *P. bilaiae* NRRL 67157, *P. bilaiae* NRRL 67158, or *P. bilaiae* NRRL 67159.

The present disclosure extends to the progeny of *P. bilaiae* NRRL B-67154, *P. bilaiae* NRRL B-67155, *P. bilaiae* NRRL B-67156, *P. bilaiae* NRRL B-67157, *P. bilaiae* NRRL B-67158, and/or *P. bilaiae* NRRL B-67159 and to modified microbial strains derived from *P. bilaiae* NRRL B-67154, *P. bilaiae* NRRL B-67155, *P. bilaiae* NRRL B-67156, *P. bilaiae* NRRL B-67157, *P. bilaiae* NRRL B-67158, and/or *P. bilaiae* NRRL B-67159.

Progeny of *P. bilaiae* NRRL B-67154, *P. bilaiae* NRRL B-67155, *P. bilaiae* NRRL B-67156, *P. bilaiae* NRRL B-67157, *P. bilaiae* NRRL B-67158, and/or *P. bilaiae* NRRL B-67159 may be produced using any suitable method(s), including, but not limited to, protoplast fusion, traditional breeding programs (e.g., backcrossing, inbreeding, etc.) and combinations thereof. In some embodiments, the progeny is born of a cross between two of *P. bilaiae* NRRL B-67154, *P. bilaiae* NRRL B-67155, *P. bilaiae* NRRL B-67156, *P. bilaiae* NRRL B-67157, *P. bilaiae* NRRL B-67158, and *P. bilaiae* NRRL B-67159. In some embodiments, the progeny is born of a cross between one of *P. bilaiae* NRRL B-67154, *P. bilaiae* NRRL B-67155, *P. bilaiae* NRRL B-67156, *P. bilaiae* NRRL B-67157, *P. bilaiae* NRRL B-67158, and *P. bilaiae* NRRL B-67159 and another fungal strain capable of converting insoluble phosphate into a soluble form of phosphate. In some embodiments, the progeny is born of a cross between one of *P. bilaiae* NRRL B-67154, *P. bilaiae* NRRL B-67155, *P. bilaiae* NRRL B-67156, *P. bilaiae* NRRL B-67157, *P. bilaiae* NRRL B-67158, and *P. bilaiae* NRRL B-67159 and a fungal strain incapable of converting insoluble phosphate into a soluble form of phosphate.

Modified microbial strains derived from *P. bilaiae* NRRL B-67154, *P. bilaiae* NRRL B-67155, *P. bilaiae* NRRL B-67156, *P. bilaiae* NRRL B-67157, *P. bilaiae* NRRL B-67158, and/or *P. bilaiae* NRRL B-67159 may be produced using suitable method(s), including, but not limited to, chemical or other form of induced mutation to a polynucleotide within any genome within *P. bilaiae* NRRL B-67154, *P. bilaiae* NRRL B-67155, *P. bilaiae* NRRL B-67156, *P. bilaiae* NRRL B-67157, *P. bilaiae* NRRL B-67158, or *P. bilaiae* NRRL B-67159; the insertion or deletion of one or more nucleotides within any genome within *P. bilaiae* NRRL B-67154, *P. bilaiae* NRRL B-67155, *P. bilaiae* NRRL B-67156, *P. bilaiae* NRRL B-67157, *P. bilaiae* NRRL B-67158, or *P. bilaiae* NRRL B-67159, or combinations thereof; an inversion of at least one segment of DNA within any genome within *P. bilaiae* NRRL B-67154, *P. bilaiae* NRRL B-67155, *P. bilaiae* NRRL B-67156, *P. bilaiae* NRRL B-67157, *P. bilaiae* NRRL B-67158, or *P. bilaiae* NRRL B-67159; a rearrangement of any genome within *P. bilaiae* NRRL B-67154, *P. bilaiae* NRRL B-67155, *P. bilaiae* NRRL B-67156, *P. bilaiae* NRRL B-67157, *P. bilaiae* NRRL B-67158, or *P. bilaiae* NRRL B-67159; generalized or specific transduction of homozygous or heterozygous polynucleotide segments into any genome within *P. bilaiae* NRRL B-67154, *P. bilaiae* NRRL B-67155, *P. bilaiae* NRRL B-67156, *P. bilaiae* NRRL B-67157, *P. bilaiae* NRRL B-67158, or *P. bilaiae* NRRL B-67159; introduction of one or more phage into any genome of *P. bilaiae* NRRL B-67154, *P. bilaiae* NRRL B-67155, *P. bilaiae* NRRL B-67156, *P. bilaiae* NRRL B-67157, *P. bilaiae* NRRL B-67158, or *P. bilaiae* NRRL B-67159; transformation of *P. bilaiae* NRRL B-67154, *P. bilaiae* NRRL B-67155, *P. bilaiae* NRRL B-67156, *P. bilaiae* NRRL B-67157, *P. bilaiae* NRRL B-67158, or *P. bilaiae* NRRL B-67159 resulting in the introduction into *P. bilaiae* NRRL B-67154, *P. bilaiae* NRRL B-67155, *P. bilaiae* NRRL B-67156, *P. bilaiae* NRRL B-67157, *P. bilaiae* NRRL B-67158, or *P. bilaiae* NRRL B-67159 of stably replicating autonomous extrachromosomal DNA; any change to any genome or to the total DNA composition within *P. bilaiae* NRRL B-67154, *P. bilaiae* NRRL B-67155, *P. bilaiae* NRRL B-67156, *P. bilaiae* NRRL B-67157, *P. bilaiae* NRRL B-67158, or *P. bilaiae* NRRL B-67159 as a result of conjugation with any different microbial strain; and any combination of the foregoing.

Fungal strains of the present disclosure may be cultured using any suitable method(s), including, but not limited to, liquid-state fermentation and solid-state fermentation. See, generally, Cunningham et al., CAN. J. BOT. 68:2270 (1990); Friesen et al., APPL. MICROBIOL. BIOTECH. 68:397 (2005).

Fungal strains of the present disclosure may be harvested during any suitable growth phase. In some embodiments, the fungal strain is allowed to reach the stationary growth phase prior to harvesting. In some embodiments, the fungal strain is harvested as vegetative cells. In some embodiments, the fungal strain is harvested as spores.

Fungal strains of the present disclosure may be harvested and/or concentrated using any suitable method(s), including, but not limited to, centrifugation (e.g., density gradient centrifugation, disc stack centrifugation, tubular bowl centrifugation), coagulation, decanting, felt bed collection, filtration (e.g., drum filtration, sieving, ultrafiltration), flocculation, impaction and trapping (e.g., cyclone spore trapping, liquid impingement).

The present disclosure also provides biologically pure cultures of the fungal strains described herein. In some embodiments, at least 95, 96, 97, 98, 99, 99.5, 99.6, 99.7, 99.8, or 99.9% of subcultures taken from the culture exhibit a genotype that is at least 95, 96, 97, 98, 99%, 99.1%, 99.2%, 99.3%, 99.4%, 99.5%, 99.55%, 99.6%, 99.65%, 99.7%, 99.75%, 99.8%, 99.85%, 99.9%, 99.95%, or 100% identical to that of *P. bilaiae* NRRL B-67154, *P. bilaiae* NRRL B-67155, *P. bilaiae* NRRL B-67156, *P. bilaiae* NRRL B-67157, *P. bilaiae* NRRL B-67158, and/or *P. bilaiae* NRRL B-67159. In some embodiments, the culture is a biologically pure culture of *P. bilaiae* NRRL B-67154, *P. bilaiae* NRRL B-67155, *P. bilaiae* NRRL B-67156, *P. bilaiae* NRRL B-67157, *P. bilaiae* NRRL B-67158, or *P. bilaiae* NRRL B-67159.

It is to be understood that cultures of the present invention may comprise vegetative cells and/or dormant spores. According to some embodiments, at least 1, 5, 10, 15, 20, 25, 30, 35, 40, 45, 50, 55, 60, 65, 70, 75, 80, 85, 90, 95, 96, 97, 98, 99% or more of the microbes in a culture of the present disclosure are present as vegetative cells. According to some embodiments, at least 1, 5, 10, 15, 20, 25, 30, 35, 40, 45, 50, 55, 60, 65, 70, 75, 80, 85, 90, 95, 96, 97, 98, 99% or more of the microbes in a culture of the present disclosure are present as spores. Fungal strains and cultures of the present disclosure may be formulated into any suitable type of composition.

In some embodiments, the present disclosure provides inoculant compositions comprising one or more fungal strains of the present disclosure in a carrier.

Fungal strains and cultures of the present disclosure may be incorporated into any suitable inoculant composition, including, but not limited to, inoculant compositions as described in International Patent Application Nos. PCT/US2016/050529 (filed Sep. 7, 2016); PCT/US2016/050647 (filed Sep. 8, 2016); PCT/US2016/067714 (filed Dec. 20, 2016); and PCT/US2016/067745 (filed Dec. 20, 2016); U.S. Provisional Patent No. 62/343,217 (filed May 31, 2016); 62/347,773 (filed Jun. 9, 2016); 62/347,785 (filed Jun. 9, 2016); 62/347,794 (filed Jun. 9, 2016); 62/347,805 (filed Jun. 9, 2016); and 62/436,529 (filed Dec. 20, 2016).

Fungal strains of the present disclosure may be incorporated into inoculant compositions in any suitable amount/concentration. The absolute value of the amount/concentration that is/are sufficient to cause the desired effect(s) may be affected by factors such as the type, size and volume of material to which the composition will be applied and storage conditions (e.g., temperature, relative humidity, duration). Those skilled in the art will understand how to select an effective amount/concentration using routine dose-response experiments.

In some embodiments, inoculant compositions of the present disclosure comprise one or more fungal strains of the present disclosure in an amount ranging from about $1\times10^1$ to about $1\times10^{15}$ colony-forming units (cfu) per gram and/or milliliter of inoculant composition. For example, inoculant compositions of the present disclosure may comprise about $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$ or more cfu of P. bilaiae NRRL B-67154, P. bilaiae NRRL B-67155, P. bilaiae NRRL B-67156, P. bilaiae NRRL B-67157, P. bilaiae NRRL B-67158, and/or P. bilaiae NRRL B-67159 cells/spores per gram and/or milliliter of inoculant composition. In some embodiments, inoculant compositions of the present disclosure comprise at least $1\times10^4$, $1\times10^5$, $1\times10^6$, $1\times10^7$, $1\times10^8$, $1\times10^9$, $1\times10^{10}$, $1\times10^{11}$, $1\times10^{12}$ cfu of one or more fungal strains of the present disclosure per gram and/or milliliter of inoculant composition.

In some embodiments, cells/spores of one or more fungal strains of the present disclosure comprises about 0.1 to about 95% (by weight) of the inoculant composition. For example, P. bilaiae NRRL B-67154, P. bilaiae NRRL B-67155, P. bilaiae NRRL B-67156, P. bilaiae NRRL B-67157, P. bilaiae NRRL B-67158, and/or P. bilaiae NRRL B-67159 cells/spores may comprise about 0.1, 0.2, 0.3, 0.4, 0.5, 0.6, 0.7, 0.8, 0.9, 1, 1.25, 1.5, 1.75, 2, 2.25, 2.5, 2.75, 3, 3.25, 3.5, 3.75, 4, 4.25, 4.5, 4.75, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95% or more (by weight) of the inoculant composition. In some embodiments, P. bilaiae NRRL B-67154, P. bilaiae NRRL B-67155, P. bilaiae NRRL B-67156, P. bilaiae NRRL B-67157, P. bilaiae NRRL B-67158, and/or P. bilaiae NRRL B-67159 comprise about 1 to about 25%, about 5 to about 20%, about 5 to about 15%, about 5 to about 10% or about 8 to about 12% (by weight) of the inoculant composition.

As noted above, and as shown in the Examples below, P. bilaiae NRRL B-67154, P. bilaiae NRRL B-67155, P. bilaiae NRRL B-67156, P. bilaiae NRRL B-67157, P. bilaiae NRRL B-67158, and P. bilaiae NRRL B-67159 are capable of converting insoluble phosphate into a soluble form of phosphate.

The aforementioned utility is not limited to P. bilaiae NRRL B-67154, P. bilaiae NRRL B-67155, P. bilaiae NRRL B-67156, P. bilaiae NRRL B-67157, P. bilaiae NRRL B-67158, and P. bilaiae NRRL B-67159. Progeny of P. bilaiae NRRL B-67154, P. bilaiae NRRL B-67155, P. bilaiae NRRL B-67156, P. bilaiae NRRL B-67157, P. bilaiae NRRL B-67158, and/or P. bilaiae NRRL B-67159 and modified microbial strains derived from P. bilaiae NRRL B-67154, P. bilaiae NRRL B-67155, P. bilaiae NRRL B-67156, P. bilaiae NRRL B-67157, P. bilaiae NRRL B-67158, and/or P. bilaiae NRRL B-67159 may also be capable of solubilizing phosphate. Those skilled in the art will understand how to determine whether a given strain is capable of solubilizing phosphate using routine experiments.

Accordingly, in some embodiments, inoculant compositions of the present disclosure comprise one or more phosphate-solubilizing progeny of P. bilaiae NRRL B-67154, P. bilaiae NRRL B-67155, P. bilaiae NRRL B-67156, P. bilaiae NRRL B-67157, P. bilaiae NRRL B-67158, and/or P. bilaiae NRRL B-67159 (e.g., an elite phosphate-solubilzing inbred strain having a whole genome sequence that is at 99, 99.1, 99.2, 99.3, 99.4, 99.5, 99.6, 99.7, 99.8 or 99.9% identical to that of P. bilaiae NRRL B-67154, P. bilaiae NRRL B-67155, P. bilaiae NRRL B-67156, P. bilaiae NRRL B-67157, P. bilaiae NRRL B-67158, and/or P. bilaiae NRRL B-67159) and/or one or more phosphate-solubilizing modified microbial strains derived from P. bilaiae NRRL B-67154, P. bilaiae NRRL B-67155, P. bilaiae NRRL B-67156, P. bilaiae NRRL B-67157, P. bilaiae NRRL B-67158, and/or P. bilaiae NRRL B-67159 (e.g., a modified microbial strain that solubilizes phosphate and has a whole genome sequence that is at least 99, 99.1, 99.2, 99.3, 99.4, 99.5, 99.6, 99.7, 99.8 or 99.9% identical to that of P. bilaiae NRRL B-67154, P. bilaiae NRRL B-67155, P. bilaiae NRRL B-67156, P. bilaiae NRRL B-67157, P. bilaiae NRRL B-67158, and/or P. bilaiae NRRL B-67159).

In some embodiments, inoculant compositions of the present disclosure comprise one or more fungal strains of the present disclosure in an effective amount/concentration for increasing the amount/concentration of soluble phosphate when the inoculant composition is introduced into a medium that comprises insoluble phosphate. In some embodiments, inoculant compositions of the present disclosure comprise one or more fungal strains of the present disclosure in an amount/concentration sufficient to increase the amount/concentration of soluble phosphate by at least 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 225, 250% or more when the inoculant composition is introduced into the medium. For example, in some embodiments, inoculant compositions of the present disclosure comprise cells/spores of P. bilaiae NRRL B-67154, P. bilaiae NRRL B-67155, P. bilaiae NRRL B-67156, P. bilaiae NRRL B-67157, P. bilaiae NRRL B-67158, and/or P. bilaiae NRRL B-67159 in an amount/concentration effective to increase the amount/concentration of soluble phosphate in a medium by at least about 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 225 or 250% when the inoculant composition is introduced into the medium.

Inoculant compositions of the present disclosure may comprise any suitable carrier(s). Selection of appropriate carrier materials will depend on the intended application(s) and the microorganism(s) present in the inoculant composition. In some embodiments, the carrier material(s) will be selected to provide an inoculant composition in the form of a liquid, gel, slurry, or solid. In some embodiments, the carrier will consist essentially of or consist of one or more stabilizing compounds.

In some embodiments, the inoculant composition comprises one or more solid carriers. According to some embodiments, the inoculant composition comprises one or more powders (e.g., wettable powders) and/or granules. Non-limiting examples of solid carriers include clays (e.g., attapulgite clays, montmorillonite clay, etc.), peat-based powders and granules, freeze-dried powders, spray-dried powders, spray-freeze-dried powders and combinations thereof.

In some embodiments, the inoculant composition comprises one or more liquid and/or gel carriers. According to some embodiments, the inoculant composition comprises one or more non-aqueous solvents. According to some embodiments, the inoculant composition comprises one or more aqueous solvents (e.g., water). According to some embodiments, an aqueous solvent, such as water, may be combined with a co-solvent, such as ethyl lactate, methyl soyate/ethyl lactate co-solvent blends (e.g., STEPOSOL™, Stepan), isopropanol, acetone, 1,2-propanediol, n-alkylpyrrolidones (e.g., AGSOLEX™ wetting agents; Ashland, Inc., Covington, Ky.), petroleum based-oils (e.g., AROMATIC™ and SOLVESSO™ fluids; ExxonMobil Chemical Company, Spring, Tex.), isoparrafinic hyydrocarbons (e.g., ISOPAR™ fluids; ExxonMobil Chemical Company, Spring, Tex.), cycloparaffinic hydrocarbons (e.g., NAPPAR™ 6; ExxonMobil Chemical Company, Spring, Tex.), mineral spirits (e.g., VARSOL™; ExxonMobil Chemical Company, Spring, Tex.), and mineral oils (e.g., paraffin oil). According to some embodiments, the inoculant composition comprises one or more inorganic solvents, such as decane, dodecane, hexylether and nonane. According to some embodiments, the inoculant composition comprises one or more organic solvents, such as acetone, dichloromethane, ethanol, hexane, methanol, propan-2-ol and trichloroethylene. Non-limiting examples of liquid/gel carriers include oils (e.g., mineral oil, olive oil, peanut oil, soybean oil, sunflower oil), polyethylene glycols (e.g., PEG 200, PEG 300, PEG 400, etc.), propylene glycols (e.g., PPG-9, PPG-10, PPG-17, PPG-20, PPG-26, etc.), ethoxylated alcohols (e.g., TOMADOL® (Air Products and Chemicals, Inc., Allentown, Pa.), TERGITOL™ 15-S surfactants such as TERGITOL™ 15-S-9 (The Dow Chemical Company, Midland, Mich.), etc.), isoparrafimc hyydrocarbons (e.g., ISOPAR™, ISOPAR™ L, ISOPAR™ M, ISOPAR™ V; ExxonMobil Chemical Company, Spring, Tex.), pentadecane, polysorbates (e.g. polysorbate 20, polysorbate 40, polysorbate 60, polysorbate 80, etc.), silicones (siloxanes, trisiloxanes, etc.) and combinations thereof.

Inoculant compositions of the present disclosure may comprise any suitable stabilizing compound(s), including, but not limited to, maltodextrins, monosaccharides, disaccharides, oligosaccharides, sugar alcohols, humic acids, fulvic acids, malt extracts, peat extracts, betaines, prolines, sarcosines, peptones, skim milks, oxidation control components, hygroscopic polymers and UV protectants.

In some embodiments, the inoculant composition comprises one or more maltodextrins (e.g., one or more maltodextrins having a dextrose equivalent value (DEV) of about 3, 4, 5, 6, 7, 8, 9, 10, 11, 12, 13, 14, 15, 16, 17, 18, 19, 20, 21, 22, 23, 24, or 25). According to some embodiments, the inoculant composition comprises one or more maltodextrins having a DEV of about 5 to about 6, 7, 8, 9, 10, 11, 12, 14, 15, 16, 17, 18, 19 or 20, about 10 to about 11, 12, 14, 15, 16, 17, 18, 19 or 20, or about 15 to about 16, 17, 18, 19 or 20. According to some embodiments, the inoculant composition comprises a combination of maltodextrins having a DEV of about 5 to about 6, 7, 8, 9, 10, 11, 12, 14, 15, 16, 17, 18, 19 or 20, about 10 to about 11, 12, 14, 15, 16, 17, 18, 19 or 20, or about 15 to about 16, 17, 18, 19 or 20. Non-limiting examples of maltodextrins include MALTRIN® M040 (DEV=5; molecular weight=3600; Grain Processing Corporation, Muscatine, Iowa), MALTRIN® M100 (DEV=10; molecular weight=1800; Grain Processing Corporation, Muscatine, Iowa), MALTRIN® M150 (DEV=15; molecular weight=1200; Grain Processing Corporation, Muscatine, Iowa), MALTRIN® M180 (DEV=18; molecular weight=1050; Grain Processing Corporation, Muscatine, Iowa), MALTRIN® M200 (DEV=20; molecular weight=900; Grain Processing Corporation, Muscatine, Iowa), MALTRIN® M250 (DEV=25; molecular weight=720; Grain Processing Corporation, Muscatine, Iowa); MALTRIN QD® M580 (DEV=16.5-19.9; Grain Processing Corporation, Muscatine, Iowa); MALTRIN QD® M585 (DEV=15.0-19.9; Grain Processing Corporation, Muscatine, Iowa); MALTRIN QD® M600 (DEV=20.0-23.0; Grain Processing Corporation, Muscatine, Iowa); GLOBE® Plus 15 DE (Ingredion Inc., Westchester, Ill.); and combinations thereof.

In some embodiments, the inoculant composition comprises one or more monosaccharides (e.g., allose, altrose, arabinose, fructose, galactose, glucose, gulose, iodose, lyxose, mannose, ribose, talose, threose and/or xylose). According to some embodiments, the inoculant composition comprises glucose. According to some embodiments, the inoculant composition does not comprise glucose.

In some embodiments, the inoculant composition comprises one or more disaccharides (e.g., cellobiose, chitobiose, gentiobiose, gentiobiulose, isomaltose, kojibiose, lactose, lactulose, laminaribiose, maltose (e.g., maltose monohydrate, anhydrous maltose), maltulose, mannobiose, melibiose, melibiulose, nigerose, palatinose, rutinose, rutinulose, sophorose, sucrose, trehalose, turanose and/or xylobiose). According to some embodiments, the inoculant composition comprises maltose. According to some embodiments, the inoculant composition does not comprise maltose. According to some embodiments, the inoculant composition comprises trehalose. According to some embodiments, the inoculant composition does not comprise trehalose.

In some embodiments, the inoculant composition comprises one or more oligosaccharides (e.g., fructo-oligosaccharides, galacto-oligosaccharides, mannon-oligosaccharides and/or raffinose).

In some embodiments, the inoculant composition comprises one or more sugar alcohols (e.g., arabitol, erythritol, fucitol, galactitol, glycerol, iditol, inositol, isomalt, lactitol, maltitol, maltotetraitol, maltotriitol, mannitol, polyglycitol, ribitol, sorbitol, threitol, volemitol and/or xylitol).

In some embodiments, the inoculant composition comprises one or more humic acids (e.g., one or more leonardite humic acids, lignite humic acids, peat humic acids and water-extracted humic acids). In some embodiments, the inoculant composition comprises ammonium humate, boron humate, potassium humate and/or sodium humate. In some embodiments, one or more of ammonium humate, boron humate, potassium humate and sodium humate is/are excluded from the inoculant composition. Nonlimiting examples of humic acids that may be useful in embodiments of the present disclosure include MDL Number MFCD00147177 (CAS Number 1415-93-6), MDL Number MFCD00135560 (CAS Number 68131-04-4), MDL Number MFCS22495372 (CAS Number 68514-28-3), CAS Number 93924-35-7, and CAS Number 308067-45-0.

In some embodiments, the inoculant composition comprises one or more fulvic acids (e.g., one or more leonardite fulvic acids, lignite fulvic acids, peat fulvic acids and/or water-extracted fulvic acids). In some embodiments, the inoculant composition comprises ammonium fulvate, boron fulvate, potassium fulvate and/or sodium fulvate. In some embodiments, one or more of ammonium fulvate, boron fulvate, potassium fulvate and sodium fulvate is/are excluded from inoculant compositions of the present disclosure. Nonlimiting examples of fulvic acids that may be useful in embodiments of the present disclosure include MDL Number MFCD09838488 (CAS Number 479-66-3).

In some embodiments, the inoculant composition comprises one or more betaines (e.g., trimethylglycine).

In some embodiments, the inoculant composition comprises one or more peptones (e.g., bacterial peptones, meat peptones, milk peptones, vegetable peptones and yeast peptones).

In some embodiments, the inoculant composition comprises one or more oxidation control components (e.g., one or more antioxidants and/or oxygen scavengers). According to some embodiments, the inoculant composition comprises one or more oxygen scavengers, such as ascorbic acid, ascorbate salts, catechol and/or sodium hydrogen carbonate. According to some embodiments, the inoculant composition comprises one or more antioxidants, such as ascorbic acid, ascorbyl palmitate, ascorbyl stearate, calcium ascorbate, carotenoids, lipoic acid, phenolic compounds (e.g., flavonoids, flavones, flavonols), potassium ascorbate, sodium ascorbate, thiols (e.g., glutathione, lipoic acid, N-acetyl cysteine), tocopherols, tocotrienols, ubiquinone and/or uric acid. Non-limiting examples of antioxidants include those that are soluble in the cell membrane (e.g., alpha tocopherol (vitamin E), ascorbyl palmitate) and those that are soluble in water (e.g., ascorbic acid and isomers or ascorbic acid, sodium or potassium salts of ascorbic acid or isomers or ascorbic acid, glutathione, sodium or potassium salts of glutathione). In some embodiments, use of a membrane-soluble antioxidant necessitates the addition of one or more surfactants to adequately disperse the antioxidant within the inoculant composition. According to some embodiments, the inoculant composition is/comprises ascorbic acid and/or glutathione.

In some embodiments, the inoculant composition comprises one or more hygroscopic polymers (e.g., hygroscopic agars, albumins, alginates, carrageenans, celluloses, gums (e.g., cellulose gum, guar gum, gum arabic, gum combretum, xantham gum), methyl celluloses, nylons, pectins, polyacrylic acids, polycaprolactones, polycarbonates, polyethylene glycols (PEG), polyethylenimines (PEI), polylactides, polymethylacrylates (PMA), polyurethanes, polyvinyl alcohols (PVA), polyvinylpyrrolidones (PVP), propylene glycols, sodium carboxymethyl celluloses and/or starches). Non-limiting examples of polymers include AGRIMER™ polymers (e.g., 30, AL-10 LC, AL-22, AT/ATF, VA 3E, VA 31, VA 5E, VA 51, VA 6, VA 6E, VA 7E, VA 71, VEMA AN-216, VEMA AN-990, VEMA AN-1200, VEMA AN-1980, VEMA H-815MS; Ashland Specialty Ingredients, Wilmington, Del.), EASYSPERSE™ polymers (Ashland Specialty Ingredients, Wilmington, Del.); DISCO™ AG polymers (e.g., L-250, L-280, L-285, L-286, L-320, L-323, L-517, L-519, L-520, L800; Incotec Inc, Salinas, Calif.), KELZAN® polymers (Bri-Chem Supply Ltd., Calgary, Alberta, Calif.), TICAXAN® xanthan powders, such as PRE-HYDRATED® TICAXAN® Rapid-3 Powder (TIC Gums, White Marsh, Md.) and combinations thereof. Additional examples of polymers may be found in Pouci, et al. AM. J. AGRIC. BIOL. Sci. 3(1):299 (2008).

In some embodiments, the inoculant composition comprises one or more UV protectants (e.g., one or more aromatic amino acids (e.g., tryptophan, tyrosine), carotenoids, cinnamates, lignosulfonates (e.g., calcium lignosulfonate, sodium lignosulfonate), melanins, mycosporines, polyphenols and/or salicylates). Non-limiting examples of UV protectants include Borregaard LignoTech™ lignosulfonates (e.g., Borresperse 3A, Borresperse CA, Borresperse NA, Marasperse AG, Norlig A, Norlig 11D, Ufoxane 3A, Ultrazine NA, Vanisperse CB; Borregaard Lignotech, Sarpsborg, Norway) and combinations thereof.

Inoculant compositions of the present disclosure may comprise any suitable excipient(s), including, but not limited to, dispersants, drying agents, anti-freezing agents, flowability agents, safeners, anti-settling agents, pH buffers and adhesives.

Inoculant compositions of the present disclosure may comprise any suitable dispersant(s), including, but not limited to, surfactants and wetting agents. Selection of appropriate dispersants will depend on the intended application(s) and the microorganism(s) present in the inoculant composition. In general, the dispersant(s) will have low toxicity for the microorganism(s) in the inoculant composition and for the medium(s) to which the inoculant composition is to be applied. Non-limiting examples of dispersants include Atlox™ (e.g., 4916, 4991; Croda International PLC, Edison, N.J.), Atlox METASPERSE™ (Croda International PLC, Edison, N.J.), BIO-SOFT® (e.g., N series, such as N1-3, N1-7, N1-5, N1-9, N23-3, N2.3-6.5, N25-3, N25-7, N25-9, N91-2.5, N91-6, N91-8; Stepan Company, Northfield, Ill.), MAKON® nonionic surfactants (e.g., DA-4, DA-6 and DA-9; Stepan Company, Northfield, Ill.), MORWET® powders (Akzo Nobel Surface Chemistry LLC, Chicago, Ill.), MULTIWET™ surfactants (e.g., MO-85P-PW-(AP); Croda International PLC, Edison, N.J.), SILWET® L-77 (Helena. Chemical Company, Collierville, Tenn.), SPAN™ surfactants (e.g., 20, 40, 60, 65, 80 and 85; Croda Inc., Edison N.J.), TAMOL™ dispersants (The Dow Chemical Company, Midland, Mich.), TERGITOL™ surfactants (e.g., TMN-6 and TMN-100X; The Dow Chemical Company, Midland, Mich.), TERSPERSE surfactants (e.g., 2001, 2020, 2100, 2105, 2158, 2700, 4894 and 4896; Hunstman Corp., The Woodlands, Tex.), TRITON™ surfactants (e.g., X-100; The Dow Chemical Company, Midland, Mich.), TWEEN® surfactants (e.g., TWEEN® 20, 21, 22, 23, 28, 40, 60, 61, 65, 80, 81 and 85; Croda International PLC, Edison, N.J.) and combinations thereof. In some embodiments, inoculant compositions of the present disclosure comprise one or more anionic surfactants. According to some embodiments, the inoculant composition comprises one or more water-soluble anionic surfactants and/or one or more water-insoluble anionic surfactants, optionally one or more anionic surfactants selected from the group consisting of alkyl carboxylates (e.g., sodium stearate), alkyl sulfates (e.g., alkyl lauryl sulfate, sodium lauryl sulfate), alkyl ether sulfates, alkyl amido ether sulfates, alkyl aryl polyether sulfates, alkyl aryl sulfates, alkyl aryl sulfonates, alkyl sulfonates, alkyl amide sulfonates, alkyl aryl sulfonates, alkyl benzene sulfonates, alkyl diphenyloxide sulfonate, alpha-olefin sulfonates, alkyl naphthalene sulfonates, paraffin sulfonates, alkyl sulfosuccinates, alkyl ether sulfosuccinates, alkylamide sulfosuccinates, alkyl sulfosuccinamates, alkyl sulfoacetates, alkyl phosphates, alkyl ether phosphates, acyl sarconsinates, acyl isethionates, N-acyl taurates, N-acyl-N-alkyltaurates, benzene sulfonates, cumene sulfonates, dioctyl sodium sulfosuccinate, ethoxylated sulfosuccinates, lignin sulfonates, linear alkylbenzene sulfonates, monoglyceride sulfates, perfluorobutanesulfonate, perfluorooctanesulfonate, phosphate ester, styrene acrylic polymers, toluene sulfonates and xylene sulfonates.

In some embodiments, inoculant compositions of the present disclosure comprise one or more cationic surfactants. According to some embodiments, the inoculant composition comprises one or more pH-dependent amines and/or one or more quaternary ammonium cations, optionally one or more cationic surfactants selected from the group consisting of alkyltrimethylammonium salts (e.g., cetyl trimethylammonium bromide, cetyl trimethylammonium chloride), cetylpyridinium chloride, benzalkonium chloride, benzethonium chloride, 5-Bromo-5-nitro-1,3-dioxane, dimethyldioctadecylammonium chloride, cetrimonium bromide, dioctadecyl dimethylammonium bromide and/or octenidine dihydrochloride.

In some embodiments, inoculant compositions of the present disclosure comprise one or more nonionic surfactants. According to some embodiments, the inoculant composition comprises one or more water-soluble nonionic surfactants and/or one or more water-insoluble nonionic surfactants, optionally one or more nonionic surfactants selected from the group consisting of alcohol ethoxylates (e.g., TERGITOL™ 15-S surfactants, such as TERGITOL™ 15-S-9 (The Dow Chemical Company, Midland, Mich.)), alkanolamides, alkanolamine condensates, carboxylic acid esters, cetostearyl alcohol, cetyl alcohol, cocamide DEA, dodecyldimethylamine oxides, ethanolamides, ethoxylates of glycerol ester and glycol esters, ethylene oxide polymers, ethylene oxide-propylene oxide copolymers, glucoside alkyl ethers, glycerol alkyl ethers, glycerol esters, glycol alkyl ethers (e.g., polyoxyethylene glycol alkyl ethers, polyoxypropylene glycol alkyl ethers), glycol alkylphenol ethers (e.g., polyoxyethylene glycol alkylphenol ethers), glycol esters, monolaurin, pentaethylene glycol monododecyl ethers, poloxamer, polyamines, polyglycerol polyricinoleate, polysorbate, polyoxyethylenated fatty acids, polyoxyethylenated mercaptans, polyoxyethylenated polyoxyproylene glycols, polyoxyethylene glycol sorbitan alkyl esters, polyethylene glycol-polypropylene glycol copolymers, polyoxyethylene glycol octylphenol ethers, polyvinyl pynolidones, sugar-based alkyl polyglycosides, sulfoanylamides, sorbitan fatty acid alcohol ethoxylates, sorbitan fatty acid ester ethoxylates, sorbitan fatty acid ester and/or tertiary acetylenic glycols.

In some embodiments, inoculant compositions of the present disclosure comprise at least one nonionic surfactant. According to some embodiments, the inoculant composition comprises at least one water insoluble nonionic surfactant and at least one water soluble nonionic surfactant. In some embodiments, inoculant compositions of the present disclosure comprise a combination of nonionic surfactants having hydrocarbon chains of substantially the same length.

In some embodiments, inoculant compositions of the present disclosure comprise one or more zwitterionic surfactants. According to some embodiments, the inoculant composition comprises one or more betaines and/or one or more sultaines, optionally one or more zwitterionic surfactants selected from the group consisting of 3[(3-Cholamidopropyl)dimethylammonio]-1-propanesulfonate, cocamidopropyl betaine, cocamidopropyl hydroxysultaine, phosphatidylserine, phosphatidylethanolamine, phosphatidylcholine and/or one or more sphingomyelins.

In some embodiments, inoculant compositions of the present disclosure comprise one or more soaps and/or organosilicone surfactants. According to some embodiments, the inoculant composition comprises one or more alkali metal salts of fatty acids.

In some embodiments, inoculant compositions of the present disclosure comprise one or more wetting agents. According to some embodiments, the inoculant composition comprises one or more naphthalene sulfonates, optionally one or more alkyl naphthalene sulfonates (e.g., sodium alkyl naphthalene sulfonate), one or more isopropyl naphthalene sulfonates (e.g., sodium isopropyl naphthalene sulfonate) and/or one or more butyl naphthalene sulfonates (e.g., sodium n-butyl naphthalene sulfonate).

Inoculant compositions of the present disclosure may comprise any suitable drying agent(s), including, but not limited to, drying powders. Non-limiting examples of drying agents include AEROSIL® hydrophobic fumed silica powders (Evonik Corporation, Parsippany, N.J.), BENTOLITE® powders (BYK-Chemie GmbH, Wesel, Germany), INCOTEC® powders (INCOTEC Inc, Salinas, Calif.), SIPERNAT® silica powders (Evonik Corporation, Parsippany, N.J.) and combinations thereof. In some embodiments, inoculant compositions of the present disclosure comprise calcium stearate, clay (e.g., attapulgite clay, montmorillonite clay), graphite, magnesium stearate, magnesium sulfate, powdered milk, silica (e.g., fumed silica, hydrophobically-coated silica, precipitated silica), soy lecithin and/or talc.

Inoculant compositions of the present disclosure may comprise any suitable anti-freezing agent(s), including, but not limited to, ethylene glycol, glycerin, propylene glycol and urea.

Inoculant compositions of the present disclosure may comprise any flowability agent to improve the lubricity of treated materials. The flowability agent may comprise one or more liquid lubricants, solid lubricants, liquid emulsions, or suspensions of solid lubricants. Non-limiting examples of flowability agents include, for example, lubricants such as fats and oils, natural and synthetic waxes, graphite, talc, fluoropolymers (e.g., polytetrafluoroethylene), and solid lubricants such as molybdenum disulfide and tungsten disulfide. In some instances, the flowability agent comprises a wax material. Non-limiting examples of wax materials that can be incorporated into the liquid treatment composition include plant and animal-derived waxes such as carnauba wax, candelilla wax, ouricury wax, beeswax, spermaceti, and petroleum derived waxes, such as paraffin wax. For example, in some instances, the flowability agent comprises carnauba wax. In some instances, the flowability agent comprises an oil. For example, the flowability agent may comprise soybean oil. Non-limiting examples of commercially available wax materials suitable for use as flowability agents include AQUAKLEAN 418 supplied by Micro Powders, Inc. (an anionic aqueous emulsion comprising extra light carnauba wax at 35% solids content).

Inoculant compositions of the present disclosure may comprise any suitable safener(s), including, but not limited to, napthalic anhydride.

Inoculant compositions of the present disclosure may comprise any suitable pH buffer(s), including, but not limited to, potassium phosphate monobasic and potassium phosphate dibasic. In some embodiments, the inoculant composition comprises one or more pH buffers selected to provide a composition having a pH of less than 10, typically from about 4.5 to about 9.5, from about 6 to about 8, or about 7.

Inoculant compositions of the present disclosure may comprise any suitable anti-settling agent(s), including, but not limited to, polyvinyl acetate, polyvinyl alcohols with different degrees of hydrolysis, polyvinylpyrrolidones, polyacrylates, acrylate-, polyol- or polyester-based paint system binders which are soluble or dispersible in water, moreover copolymers of two or more monomers such as acrylic acid, methacrylic acid, itaconic acid, maleic acid, fumaric acid, maleic anhydride, vinylpyrrolidone, ethylenically unsaturated monomers such as ethylene, butadiene, isoprene, chloroprene, styrene, divinylbenzene, ot-methylstyrene or p-methylstyrene, further vinyl halides such as vinyl chloride and vinylidene chloride, additionally vinyl esters such as vinyl acetate, vinyl propionate or vinyl stearate, moreover vinyl methyl ketone or esters of acrylic acid or methacrylic acid with monohydric alcohols or polyols such as methyl acrylate, methyl methacrylate, ethyl acrylate, ethylene methacrylate, lauryl acrylate, lauryl methacrylate, decyl acrylate, N,N-dimethylamino-ethyl methacrylate, 2-hydroxyethyl methacrylate, 2-hydroxypropyl methacrylate or glycidyl methacrylate, furthermore diethyl esters or monoesters of unsaturated dicarboxylic acids, furthermore (meth)acrylamido-N-methylol methyl ether, amides or nitriles such as acrylamide, methacrylamide, N-methylol(meth)acrylamide, acrylonitrile, methacrylonitrile, and also N-substituted maleiraides and ethers such as vinyl butyl ether, vinyl isobutyl ether or vinyl phenyl ether, and combinations thereof.

Inoculant compositions of the present disclosure may comprise any suitable adhesive(s), including, but not limited to, adhesive compositions comprising, consisting essentially of or consisting of one or more disaccharides (e.g. maltose), gums (e.g., cellulose gum, guar gum, gum arabic, gum combretum, xantham gum), maltodextrins (e.g., one or more maltodextrins (each and/or collectively) having a DEV of about 10 to about 20), monosaccharides, oils (e.g., mineral oil, olive oil, peanut oil, soybean oil and/or sunflower oil) and/or oligosaccharides.

Inoculant compositions of the present disclosure may comprise any suitable effect pigment(s). Effect pigments, which are sometimes also referred to in the art as "pearl pigments," are a class of materials that provide reflectivity, shine, and/or a pearlescent effect when applied as a coating. In some instances, the effect pigment is in the form of a powder comprising a substrate material and a metal oxide coating. For example, the effect pigment may comprise a substrate material including but not limited to talc, silicate materials (e.g., mica), clay minerals, calcium carbonate, kaolin, phlogopite, alumina, and similar substances. In some instances, the substrate material comprises a hydrophilic material. The substrate material may be coated with a semi-transparent layer of a metal oxide, including but not limited to titanium dioxide, iron oxide, chromium oxide, or zirconium oxide. Alternatively, in some instances, the effect pigment comprises metal powder or metal flakes. The metal powder or metal flakes may comprise a metal including, but not limited to aluminum, copper, silver, or bronze. In some instances, the effect pigment comprises a silicate based substrate. Non-limiting examples of particulate silicates that can be incorporated into the dry powder coating include mica coated with titanium dioxide (e.g., SUNMICA FINE WHITE 2800102, which is commercially available from Sun Chemical Corp.). Other non-limiting examples of commercially available effect pigments that can be incorporated into the dry powder include MAGNA PEARL, LUMINA and MEARLIN pigments from BASF Corporation; PHIBRO PEARL from PhibroChem; and IRIDESIUM 120 from Aakash Chemicals. In some instances, the dry powder has a mean particle size of from about 1 to about 25 microns.

Inoculant compositions of the present disclosure may comprise any growth medium suitable for culturing one or more of the microorganisms in the inoculant composition. For example, in some embodiments, inoculant compositions of the present disclosure comprise Czapek-Dox medium, glycerol yeast extract, mannitol yeast extract, potato dextrose broth and/or YEM media.

Carriers, stabilizing compounds, dispersants, drying agents, safeners, flowability agents, anti-settling agents, buffers, adhesives, etc. may be incorporated into inoculant compositions of the present disclosure in any suitable amount(s)/concentration(s). The absolute value of the amount/concentration that is/are sufficient to cause the desired effect(s) may be affected by factors such as the type, size and volume of material to which the composition will be applied, the type(s) of microorganisms in the composition, the number of microorganisms in the composition, the stability of the microorganisms in the composition and storage conditions (e.g., temperature, relative humidity, duration). Those skilled in the art will understand how to select effective amounts/concentrations using routine dose-response experiments. Guidance for the selection of appropriate amounts/concentrations can be found, for example, in International Patent Application Nos. PCT/US2016/050529 and PCT/US2016/050647 and U.S. Provisional Patent Application Nos. 62/296,798; 62/271,857; 62/347,773; 62/343,217; 62/296,784; 62/271,873; 62/347,785; 62/347,794; and 62/347,805.

In some embodiments, inoculant compositions of the present disclosure comprise one or more carriers in an amount/concentration of about 1 to about 99% or more (by weight, based upon the total weight of the inoculant composition). For example, inoculant compositions of the present disclosure may comprise about 1, 2, 3, 4, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98 or 99% (by weight) of one or more non-aqueous carriers.

In some embodiments, inoculant compositions of the present disclosure comprise one or more stabilizing compounds in an amount/concentration of about 0.0001 to about 95% or more (by weight, based upon the total of the inoculant composition). For example, inoculant compositions of the present disclosure may comprise about 0.0001 to about 0.001, about 0.001 to about 1%, about 0.25 to about 5%, about 1 to about 10%, about 5 to about 25%, about 10% to about 30%, about 20% to about 40%, about 25% to about 50%, about 30 to about 60%, about 50 to about 75%, or about 75 to about 95% (by weight), optionally about 0.0005, 0.001, 0.002, 0.003, 0.004, 0.005, 0.0075, 0.01, 0.02, 0.03, 0.04, 0.05, 0.06, 0.07, 0.08, 0.09, 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95%, of one or more maltodextrins, monosaccharides, disaccharides, sugar alcohols, humic acids, betaines, prolines, sarcosines, peptones, oxidation control components, hygroscopic polymers and/or UV protectants.

In some embodiments, inoculant compositions of the present disclosure comprise one or more stabilizing compounds at a concentration of about $1\times10^{-20}$M to about $1\times10^{-1}$M. For example, inoculant compositions of the present disclosure may comprise about $1\times10^{-15}$M to about $1\times10^{-10}$M, about $1\times10^{-14}$M to about $1\times10^{-8}$M, about $1\times10^{-14}$M to about $1\times10^{-6}$M, about $1\times10^{-12}$M to about $1\times10^{-8}$M, about $1\times10^{-12}$M to about $1\times10^{-6}$M, about $1\times10^{-10}$M to about $1\times10^{-6}$M, or about $1\times10^{-8}$M to about $1\times10^{-2}$M, optionally about $1\times10^{-20}$M, $1\times10^{-19}$M, $1\times10^{-18}$M, $1\times10^{-17}$M, $1\times10^{-16}$M, $1\times10^{-15}$M, $1\times10^{-14}$M, $1\times10^{-13}$M, $1\times10^{-12}$M, $1\times10^{-11}$M, $1\times10^{-10}$M, $1\times10^{-9}$ M, $1\times10^{-8}$M, $1\times10^{-7}$M, $1\times10^{-6}$, $1\times10^{-5}$M, $1\times10^{-4}$M, $1\times10^{-3}$M, $1\times10^{-2}$M, $1\times10^{-1}$M or more, of one or more maltodextrins, monosaccharides, disaccharides, sugar alcohols, humic acids, betaines, prolines, sarcosines, peptones, oxidation control components, hygroscopic polymers and/or UV protectants.

In some embodiments, inoculant compositions of the present disclosure comprise one or more monosaccharides in an amount/concentration of about 0.005 to about 50% (by weight) of the inoculant composition. For example, inoculant compositions of the present disclosure may comprise about/at least/less than 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.75, 1, 1.25, 1.5, 2, 2.5, 3, 3.5, 4, 4.5, 5, 5.5, 6, 6.5, 7, 7.5, 8, 8.5, 9, 10, 15, 20, 25% (by weight) of one or more monosaccharides (e.g., arabinose, fructose and/or glucose). In some embodiments, one or more monosaccharides is/are present in a concentration ranging from about $1\times10^{-20}$M to about $1\times10^{-1}$M. For example, one or more monosaccharides may be included at a concentration of about/at least/less than $1\times10^{-20}$M, $1\times10^{-19}$M, $1\times10^{-18}$M, $1\times10^{-17}$M, $1\times10^{-16}$M, $1\times10^{-15}$M, $1\times10^{-14}$M, $1\times10^{-13}$M, $1\times10^{-12}$M, $1\times10^{-11}$M, $1\times10^{-10}$M.

In some embodiments, inoculant compositions of the present disclosure comprise one or more disaccharides in an amount/concentration of about 0.005 to about 50% (by weight) of the inoculant composition. For example, inoculant compositions of the present disclosure may comprise about/at least/less than 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.75, 1, 1.25, 1.5, 2, 2.5, 3, 3.5, 4, 4.5, 5, 5.5, 6, 6.5, 7, 7.5, 8, 8.5, 9, 10, 15, 20, 25% (by weight) of one or more disaccharides (e.g., maltose, sucrose and/or trehalose). In some embodiments, one or more disaccharides is/are present in a concentration ranging from about $1\times10^{-20}$M to about $1\times10^{-1}$M. For example, one or more disaccharides may be included at a concentration of about/at least/less than $1\times10^{-20}$M, $1\times10^{-19}$M, $1\times10^{-18}$M, $1\times10^{-17}$M, $1\times10^{-16}$M, $1\times10^{-15}$M, $1\times10^{-14}$M, $1\times10^{-13}$M, $1\times10^{-12}$M, $1\times10^{-11}$M, $1\times10^{-10}$M.

In some embodiments, inoculant compositions of the present disclosure comprise one or more maltodextrins in an amount/concentration of about 0.001 to about 95% or more (by weight) of the inoculant composition. In some embodiments, the maltodextrin(s) comprise(s) about 0.001 to about 1%, about 0.25 to about 5%, about 1 to about 10%, about 5 to about 25%, about 10% to about 30%, about 20% to about 40%, about 25% to about 50%, about 50 to about 75%, or about 75 to about 95% (by weight) of the inoculant composition. For example, inoculant compositions of the present disclosure may comprise about/at least/less than 0.01, 0.02, 0.03, 0.04, 0.05, 0.06, 0.07, 0.08, 0.09, 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95% or more (by weight) of one or more maltodextrins (e.g., one or more maltodextrins (each and/or collectively) having a DEV value of about 15 to about 20).

In some embodiments, inoculant compositions of the present disclosure comprise one or more sugar alcohols in an amount/concentration of about 0.001 to about 95% or more (by weight) of the inoculant composition. In some embodiments, the sugar alcohol(s) (e.g., arabitol, mannitol, sorbitol and/or xylitol) comprise(s) about 0.001 to about 1%, about 0.25 to about 5%, about 1 to about 10%, about 5 to about 25%, about 10% to about 30%, about 20% to about 40%, about 25% to about 50%, about 50 to about 75%, or about 75 to about 95% (by weight) of the inoculant composition. For example, inoculant compositions of the present disclosure may comprise about/at least/less than 0.01, 0.02, 0.03, 0.04, 0.05, 0.06, 0.07, 0.08, 0.09, 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95% or more (by weight) of one or more sugar alcohols (e.g., arabitol, mannitol, sorbitol and/or xylitol).

In some embodiments, inoculant compositions of the present disclosure comprise one or more humic acids in an amount/concentration of about 0.001 to about 95% or more (by weight) of the inoculant composition. In some embodiments, the humic acid(s) (e.g., potassium humate) comprise(s) about 0.001 to about 1%, about 0.25 to about 5%, about 1 to about 10%, about 5 to about 25%, about 10% to about 30%, about 20% to about 40%, about 25% to about 50%, about 50 to about 75%, or about 75 to about 95% (by weight) of the inoculant composition. For example, inoculant compositions of the present disclosure may comprise about/at least/less than 0.01, 0.02, 0.03, 0.04, 0.05, 0.06, 0.07, 0.08, 0.09, 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95% or more (by weight) of one or more humic acids (e.g., potassium humate and/or sodium humate).

In some embodiments, inoculant compositions of the present disclosure comprise one or more UV protectants in an amount/concentration of about 0.0001 to about 5% or more (by weight) of the inoculant composition. In some embodiments, the UV protectant(s) (e.g., calcium lignosulfate and/or sodium lignosulfate) comprise(s) about 0.0001 to about 0.001, about 0.001 to about 1%, about 0.25 to about 5%, (by weight) of the inoculant composition. For example, inoculant compositions of the present disclosure may comprise about/at least/less than 0.0005, 0.001, 0.002, 0.003, 0.004, 0.005, 0.0075, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.75, 1, 1.25, 1.5, 2, 2.5, 3, 3.5, 4, 4.5, 5% or more (by weight) of one or more UV protectants (e.g., calcium lignosulfate and/or sodium lignosulfate).

In some embodiments, inoculant compositions of the present disclosure comprise one or more oxidation control components in an amount/concentration of about 0.0001 to about 5% or more (by weight) of the composition. For example, inoculant compositions of the present disclosure may comprise about/at least/less than 0.0005, 0.001, 0.002, 0.003, 0.004, 0.005, 0.0075, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.75, 1, 1.25, 1.5, 2, 2.5, 3, 3.5, 4, 4.5, 5% of one or more oxidation control components. In some embodiments, the amount/concentration of oxidation control components is about 0.005 to about 2% (by weight) of the composition. In some embodiments, the oxidation control component(s) is/are present in a concentration ranging from about $1\times10^{-20}$M to about $1\times10^{-1}$M. For example, one or more oxidation control components may be added at a concentration of about/at least/less than $1\times10^{-20}$M, $1\times10^{-19}$M, $1\times10^{-18}$M, $1\times10^{-17}$M, $1\times10^{-16}$M, $1\times10^{-15}$M, $1\times10^{-14}$M, $1\times10^{-13}$M, $1\times10^{-12}$M, $1\times10^{-11}$M, $1\times10^{-10}$M. In some embodiments, inoculant compositions of the present disclosure comprise one or more commercial antioxidants used in accordance with the manufacturer's recommended amounts/concentrations. In some embodiments, inoculant compositions of the present disclosure comprise one or more commercial oxygen scavengers used in accordance with the manufacturer's recommended amounts/concentrations.

In some embodiments, inoculant compositions of the present disclosure comprise one or more stabilizing compounds in an amount/concentration sufficient to ensure the fungal cells and/or spores remain viable following:

storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

desiccation by about 5, 10, 15, 20, 25, 30, 35, 40, 45, 50, 55, 60, 65, 70, 75, 80, 85, 90, 95% or more; desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

application;

application and desiccation by about 5, 10, 15, 20, 25, 30, 35, 40, 45, 50, 55, 60, 65, 70, 75, 80, 85, 90, 95% or more; and/or application and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, inoculant compositions of the present disclosure comprise one or more stabilizing compounds in an amount/concentration sufficient to ensure at least 0.01, 0.05, 0.1, 0.5, 1, 2, 3, 4, 5, 10, 15, 20, 25, 30, 35, 40, 45, 50, 55, 60, 65, 70, 75, 80, 85, 90, 95% of the fungal cells and/or spores remain viable following:

storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

desiccation by about 5, 10, 15, 20, 25, 30, 35, 40, 45, 50, 55, 60, 65, 70, 75, 80, 85, 90, 95% or more;

desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

application;

application and desiccation by about 5, 10, 15, 20, 25, 30, 35, 40, 45, 50, 55, 60, 65, 70, 75, 80, 85, 90, 95% or more; and/or application and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, inoculant compositions of the present disclosure comprise one or more stabilizing compounds in an amount/concentration sufficient to ensure at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$ or more colony-forming units of the fungal cells and/or spores remain viable per gram and/or milliliter of inoculant composition following: storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; desiccation by about 5, 10, 15, 20, 25, 30, 35, 40, 45, 50, 55, 60, 65, 70, 75, 80, 85, 90, 95% or more;

desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

application;

application and desiccation by about 5, 10, 15, 20, 25, 30, 35, 40, 45, 50, 55, 60, 65, 70, 75, 80, 85, 90, 95% or more; and/or application and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, inoculant compositions of the present disclosure comprise one or more stabilizing compounds in an amount/concentration sufficient to ensure the deliquescence relative humidity (DRH) of the inoculant composition is less than 5, 10, 15, 20, 25, 30, 35, 40, 45, 50, 55, 60, 65, 70, 75, 80, 85 or 90 at the temperature(s) at which the composition is to be stored (e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C.).

In some embodiments, inoculant compositions of the present disclosure comprise two or more stabilizing compounds that synergistically enhance the stability and/or survival of the fungal cells and/or spores.

Stabilizing compounds may be incorporated into inoculant compositions of the present disclosure in any suitable ratio(s).

In some embodiments, inoculant compositions of the present disclosure comprise one or more maltodextrins and one or more monosaccharides, disaccharides, sugar alcohols and/or humic acids in a maltodextrin:(monosaccharide, disaccharide, sugar alcohol and/or humic acid) ratio of about 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5. For example, inoculant compositions of the present disclosure may comprise one or more maltodextrins (e.g., one or more maltodextrins (each and/or collectively) having a DEV of about 15 to about 20) and one or more sugar alcohols (e.g., sorbitol and/or xylitol) and/or humic acids (e.g., potassium humate) in a maltodextrin:(sugar alcohol/humic acid) ratio of about 5:95, about 15:85, about 25:75 or about 50:50.

In some embodiments, inoculant compositions of the present disclosure comprise one or more dispersants in an amount/concentration of about 0.001 to about 25% or more (by weight) of the inoculant composition. In some embodiments, the dispersant(s) comprise(s) 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.06, 0.07, 0.08, 0.09, 0.1, 0.02, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 6, 7, 8, 9 or 10 to about 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19 or 20% (by weight) of the inoculant composition. For example, inoculant compositions of the present disclosure may comprise about 0.01, 0.02, 0.03, 0.04, 0.05, 0.06, 0.07, 0.08, 0.09, 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20% or more (by weight) of one or more dispersants (e.g., one or more surfactants and/or wetting agents).

In some embodiments, inoculant compositions of the present disclosure comprise one or more drying agents in an amount/concentration of about 0.001 to about 95% or more (by weight) of the inoculant composition. In some embodiments, the drying agent(s) comprise(s) about) 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.06, 0.07, 0.08, 0.09, 0.1, 0.02, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 6, 7, 8, 9 or 10 to about 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19 or 20% (by weight) of the inoculant composition. For example, inoculant compositions of the present disclosure may comprise about 0.01, 0.02, 0.03, 0.04, 0.05, 0.06, 0.07, 0.08, 0.09, 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95% or more (by weight) of one or more drying agents (e.g., lecithin and/or talc).

In some embodiments, the inoculant compositions of the present disclosure comprise about 0.5 to about 10 grams of drying powder per liter of inoculant composition. For example, inoculant compositions of the present disclosure may comprise about 0.5, 1, 1.25, 1.5, 1.75, 2, 2.25, 2.5, 2.75, 3, 3.25, 3.5, 3.75, 4, 4.25, 4.5, 4.75, 5, 5.5, 6, 6.5, 7, 7.5, 8, 8.5, 9, 9.5, 10 grams or more of drying powder per liter of inoculant composition.

In some embodiments, inoculant compositions of the present disclosure comprise one or more buffers in an amount/concentration of about 0.0001 to about 5% or more (by weight) of the inoculant composition. In some embodiments, the buffer(s) comprise(s) about 0.0001, 0.0002, 0.0003, 0.0004, 0.0005, 0.0006, 0.0007, 0.0008, 0.0009, 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.06, 0.07, 0.08, 0.09, 0.1, 0.02, 0.3, 0.4, 0.5, 0.6, 0.7, 0.8, 0.9, 1 to about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% (by weight) of the inoculant composition. For example, inoculant compositions of the present disclosure may comprise about 0.0005, 0.00075, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% or more (by weight) of one or more buffers (e.g., potassium phosphate monobasic and/or potassium phosphate dibasic).

In some embodiments, inoculant compositions of the present disclosure comprise one or more commercial carriers, antioxidants, oxygen scavengers, hygroscopic polymers, UV protectants, disperants, drying agents, anti-freezing agents, buffers and/or adhesives used in accordance with the manufacturer's recommended amounts/concentrations.

In some embodiments, the fungal strain(s) of the present disclosure is/are the only microbial strain(s) in inoculant compositions of the present disclosure.

In some embodiments, inoculant compositions of the present disclosure comprise one or more microorganisms in addition to the fungal strain(s) of the present disclosure. Any suitable microorganism(s) may be added. Selection of additional microbes (if any) will depend on the intended application(s).

Non-limiting examples of bacteria that may be included in inoculant compositions of the present disclosure include *Azospirillum brasilense* INTA Az-39, *Bacillus amyloliquefaciens* D747, *Bacillus amyloliquefaciens* NRRL B 50349, *Bacillus amyloliquefaciens* TJ1000, *Bacillus amyloliquefaciens* FZB24, *Bacillus amyloliquefaciens* FZB42, *Bacillus amyloliquefaciens* IN937a, *Bacillus amyloliquefaciens* IT-45, *Bacillus amyloliquefaciens* TJ1000, *Bacillus amyloliquefaciens* MBI600, *Bacillus amyloliquefaciens* BS27 (deposited as NRRL B-5015), *Bacillus amyloliquefaciens* BS2084 (deposited as NRRL B-50013), *Bacillus amyloliquefaciens* 15AP4 (deposited as ATCC PTA-6507), *Bacillus amyloliquefaciens* 3AP4 (deposited as ATCC PTA-6506), *Bacillus amyloliquefaciens* LSSA01 (deposited as NRRL B-50104), *Bacillus amyloliquefaciens* ABP278 (deposited as NRRL B-50634), *Bacillus amyloliquefaciens* 1013 (deposited as NRRL B-50509), *Bacillus amyloliquefaciens* 918 (deposited as NRRL B-50508), *Bacillus amyloliquefaciens* 22CP1 (deposited as ATCC PTA-6508) and *Bacillus amyloliquefaciens* BS18 (deposited as NRRL B-50633), *Bacillus cereus* 1-1562, *Bacillus firmus* 1-1582, *Bacillus lichenformis* BA842 (deposited as NRRL B-50516), *Bacillus lichenformis* BL21 (deposited as NRRL B-50134), *Bacillus mycoides* NRRL B-21664, *Bacillus* pumilus NRRL B 21662, *Bacillus pumilus* NRRL B-30087, *Bacillus pumilus* ATCC 55608, *Bacillus pumilus* ATCC 55609, *Bacillus pumilus* GB34, *Bacillus pumilus* KFP9F, *Bacillus pumilus* QST 2808, *Bacillus subtilis* ATCC 55078, *Bacillus subtilis* ATCC 55079, *Bacillus subtilis* MBI 600, *Bacillus subtilis* NRRL B-21661, *Bacillus subtilis* NRRL B-21665, *Bacillus subtilis* CX-9060, *Bacillus subtilis* GB03, *Bacillus subtilis* GB07, *Bacillus subtilis* QST-713, *Bacillus subtilis* FZB24, *Bacillus subtilis* D747, *Bacillus subtilis* 3BP5 (deposited as NRRL B-50510), *Bacillus thuringiensis* ATCC 13367, *Bacillus thuringiensis* GC-91, *Bacillus thuringiensis* NRRL B-21619, *Bacillus thuringiensis* ABTS-1857, *Bacillus thuringiensis* SAN 401 I, *Bacillus thuringiensis* ABG-6305, *Bacillus thuringiensis* ABG-6346, *Bacillus thuringiensis* AM65-52, *Bacillus thuringiensis* SA-12, *Bacillus thuringiensis* SB4, *Bacillus thuringiensis* ABTS-351, *Bacillus thuringiensis* HD-1, *Bacillus thuringiensis* EG 2348, *Bacillus thuringiensis* EG 7826, *Bacillus thuringiensis* EG 7841, *Bacillus thuringiensis* DSM 2803, *Bacillus thuringiensis* NB-125, *Bacillus thuringiensis* NB-176, BRADY, *Pseudomonas jessenii* PS06, *Rhizobium leguminosarum* SO12A-2 (IDAC 080305-01), *Sinorhizobium fredii* CCBAU114, *Sinorhizobium fredii* USDA 205, *Yersinia entomophaga* O82KB8 and combinations thereof, as well as microorganisms having at least at least 75, 80, 85, 90, 95, 96, 97, 97.5, 98, 98.5, 99, 99.5, 99.6, 99.7, 99.8, 99.9% or more identical to any of the aforementioned strains on the basis of 16S rDNA sequence identity.

Non-limiting examples of fungi that may be included in inoculant compositions of the present disclosure include *Gliocladium virens* ATCC 52045, *Gliocladium virens* GL-21, *Glomus infraradices* RTI-801, *Metarhizium anisopliae* F52, PENI, *Trichoderma asperellum* SKT-1, *Trichoderma asperellum* ICC 012, *Trichoderma afroviride* LC52, *Trichoderma atroviride* CNCM 1-1237, *Trichoderma fertile* JM41R, *Trichoderma gamsii* ICC 080, *Trichoderma hamatum* ATCC 52198, *Trichoderma harzianum* ATCC 52445, *Trichoderma harzianum* KRL-AG2, *Trichoderma harzianum* T-22, *Trichoderma harzianum* TH-35, *Trichoderma harzianum* T-39, *Trichoderma harzianum* ICC012, *Trichoderma reesi* ATCC 28217, *Trichoderma virens* ATCC 58678, *Trichoderma virens* G1-3, *Trichoderma virens* GL-21, *Trichoderma virens* G-41, *Trichoderma viridae* ATCC 52440, *Trichoderma viridae* ICC080, *Trichoderma viridae* TV1 and combinations thereof, as well as microorganisms having at least at least 75, 80, 85, 90, 95, 96, 97, 97.5, 98, 98.5, 99, 99.5, 99.6, 99.7, 99.8, 99.9% or more identical to any of the aforementioned strains on the basis of internal transcribed spacer (ITS) and/or cytochrome c oxidase (CO1) sequence identity.

Non-limiting examples of mycorrhizal fungi that may be included in inoculant compositions of the present disclosure include mycorrhizal strains such as *Gigaspora margarita, Glomus aggregatum, Glomus brasilianum, Glomus clarum, Glomus deserticola, Glomus etunicatum, Glomus infraradices, Glomus monosporum, Glomus mosseae, Laccaria bicolor, Laccaria laccata, Paraglomus brazilianum, Pisolithus tinctorius, Rhizopogon amylopogon, Rhizopogon fulvigleba, Rhizopogon luteolus, Rhizopogon villosuli, Scleroderma cepa* and *Scleroderma cifrinum* and combinations thereof.

Additional examples of microorganisms that may be added to inoculant compositions of the present disclosure can be found in Appendix A.

Additional microorganisms may be incorporated into inoculant compositions of the present disclosure in any suitable amount(s)/concentration(s). The absolute value of the amount/concentration that is/are sufficient to cause the desired effect(s) may be affected by factors such as the type, size and volume of material to which the compositon will be applied, the microorganisms in the composition, the number of microorganisms in the composition, the stability of the microorganisms in the composition and storage conditions (e.g., temperature, relative humidity, duration). Those skilled in the art will understand how to select an effective amount/concentration using routine dose-response experiments. Guidance for the selection of appropriate amounts/concentrations can be found, for example, in International Patent Application Nos. PCT/US2016/050529 and PCT/US2016/050647 and U.S. Provisional Patent Application Nos. 62/296,798; 62/271,857; 62/347,773; 62/343,217; 62/296,784; 62/271,873; 62/347,785; 62/347,794; and 62/347,805.

In some embodiments, one or more additional microorganisms is/are present in an amount ranging from about $1 \times 10^1$ to about $1 \times 10^{12}$ colony-forming units (cfu) per gram and/or millilitre of inoculant composition. According to some embodiments, the inoculant composition comprises about $1 \times 10^1$, $1 \times 10^2$, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$ or more cfu of one or more additional microorganisms per gram and/or milliliter of inoculant composition (e.g., about $1 \times 10^4$ to about 1 xo $10^9$ cfu/g of *Bacillus amyloliquefaciens* TJ1000 (also known as 1BE, isolate ATCC BAA-390), BRADY, *Metarhizium anisopliae* F52, PENT, *Trichoderma virens* G1-3, and/or *Yersinia entomophaga* O82KB8). In some embodiments, inoculant compositions of the present disclosure comprise at least $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$ cfu of one or more additional microorganisms per gram and/or milliliter of inoculant composition.

In some embodiments, spores from one or more additional microorganism comprise about 0.1 to about 90% (by weight) of the inoculant composition. According to some embodiments, the inoculant composition comprises about 0.1, 0.2, 0.3, 0.4, 0.5, 0.6, 0.7, 0.8, 0.9, 1, 1.25, 1.5, 1.75, 2, 2.25, 2.5, 2.75, 3, 3.25, 3.5, 3.75, 4, 4.25, 4.5, 4.75, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95% or more (by weight) of microbial spores from one or more additional microorganisms (e.g., about 10% *Bacillus amyloliquefaciens* TJ1000, *Metarhizium anisopliae* F52, *Penicillium bilaiae* ATCC 20851, *Penicillium bilaiae* RS7B-SD1 and/or *Trichoderma virens* G1-3 spores). In some embodiments, the amount/concentration of microbial spores from one or more additional microorganisms is about 1 to about 25%, about 5 to about 20%, about 5 to about 15%, about 5 to about 10% or about 8 to about 12% (by weight) of the inoculant composition.

It is to be understood that additional microorganisms in inoculant compositions of the present disclosure may comprise vegetative cells and/or dormant spores. According to some embodiments, at least 1, 5, 10, 15, 20, 25, 30, 35, 40, 45, 50, 55, 60, 65, 70, 75, 80, 85, 90, 95, 96, 97, 98, 99% or more additional microorganisms are present in inoculant compostions of the present disclosure as vegetative cells. According to some embodiments, at least 1, 5, 10, 15, 20, 25, 30, 35, 40, 45, 50, 55, 60, 65, 70, 75, 80, 85, 90, 95, 96, 97, 98, 99% or more additional microorganisms are present in inoculant compositions of the present disclosure as spores.

Inoculant compositions of the present disclosure may be formulated as any suitable type of composition. In some embodiments, inoculant compositions of the present disclosure are formulated as amorphous solids.

In some embodiments, inoculant compositions of the present disclosure are formulated as amorphous liquids.

In some embodiments, inoculant compositions of the present disclosure are formulated as wettable powders.

In some embodiments, inoculant compositions of the present disclosure are formulated as liquid compositions that are subsequently dried to produce a powder or granule. For example, in some embodiments, liquid inoculant compositions of the present disclosure are drum dried, evaporation dried, fluidized bed dried, freeze dried, spray dried, spray-freeze dried, tray dried and/or vacuum dried to produce powders/granules. Such powders/granules may be further processed using any suitable method(s), including, but not limited to, flocculation, granulation and milling, to achieve a desired particle size or physical format. The precise method(s) and parameters of processing dried powders/granules that are appropriate in a given situation may be affected by factors such as the desired particle size(s), the type, size and volume of material to which the composition will be applied, the type(s) of microorganisms in the composition, the number of microorganisms in the composition, the stability of the microorganisms in the composition and the storage conditions (e.g., temperature, relative humidity, duration). Those skilled in the art will understand how to select appropriate methods and parameters using routine experiments.

In some embodiments, inoculant compositions of the present disclosure are frozen for cryopreservation. For example, in some embodiments, liquid inoculant compositions of the present disclosure are flash-frozen and stored in a cryopreservation storage unit/facility. The precise method(s) and parameters of freezing and preserving inoculant compositions of the present disclosure that are appropriate in a given situation may be affected by factors such as the type(s) of microorganisms in the composition, the number of microorganisms in the composition, the stability of the microorganisms in the composition and the storage conditions (e.g., temperature, relative humidity, duration). Those skilled in the art will understand how to select appropriate methods and parameters using routine experiments.

Inoculant compositions of the present disclosure may be formulated as aqueous or non-aqueous compositions. In some embodiments, inoculant compositions of the present disclosure comprise no water. In some embodiments, inoculant compositions of the present disclosure comprise a trace amount of water. In some embodiments, inoculant compositions of the present disclosure comprise less than 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.25, 1.5, 1.75, 2, 2.25, 2.5, 2.75, 3, 3.25, 3.5, 3.75, 4, 4.25, 4.5, 4.75 or 5% water by weight, based upon the total weight of the composition.

In some embodiments, inoculant compositions of the present disclosure are formulated to have a pH of about 4.5 to about 9.5. In some embodiments, inoculant compositions of the present disclosure have a pH of about 6 to about 7.5. In some embodiments, inoculant compositions of the present disclosure have a pH of about 5, 5.5, 6, 6.5, 7, 7.5, 8 or 8.5.

As noted above, inoculant compositions of the present disclosure may contain a variety of carriers, stabilizers, dispersants, etc. It is to be understood that the components to be included in the inoculant composition and the order in which components are incorporated into the inoculant composition may be chosen or designed to maintain or enhance the dispersion, stability and/or survival of fungal cells/spores of the present disclosure during storage, distribution, and/or application of the inoculant composition.

It is to be understood that inoculant compositions of the present disclosure are non-naturally occurring compositions. According to some embodiments, the inoculant composition comprises one or more non-naturally occurring components. According to some embodiments, the inoculant composition comprises a non-naturally occurring combination of naturally occurring components.

The present disclosure extends to kits comprising, consisting essentially of, or consisting of two or more containers, each comprising one or more components of an inoculant composition of the present disclosure. For example, spores of *P. bilaiae* NRRL B-67154, *P. bilaiae* NRRL B-67155, *P. bilaiae* NRRL B-67156, *P. bilaiae* NRRL B-67157, *P. bilaiae* NRRL B-67158, and/or *P. bilaiae* NRRL B-67159 and the carrier may be housed in separate containers for long-term storage, then combined prior to introducing/applying the inoculant composition (in) to the desired target. Optional constituents, such as stabilizing compounds, may be added to either of the two containers or housed in one or more separate containers for long-term storage. In some embodiments, the kit further comprises one or more oxygen scavengers, such as activated carbon, ascorbic acid, iron powder, mixtures of ferrous carbonate and metal halide catalysts, sodium chloride and/or sodium hydrogen carbonate.

The containers may comprise any suitable material(s), including, but not limited to, materials that reduce the amount of light, moisture and/or oxygen that contact the inoculant composition when the container is sealed. In some embodiments, the containers comprise, consist essentially of, or consist of a material having light permeability of less than about 1, 2, 3, 4, 5, 6, 7, 8, 9, 10, 15, 20, 25, 30, 35, 40, 45, 50, 55, 60, 65, 70 or 75%. In some embodiments, the containers comprise, consist essentially of, or consist of a material having an oxygen transmission rate of less than about 5, 10, 15, 20, 25, 30, 35, 40, 45, 50, 60, 70, 80, 90, 100, 125, 150, 175, 200, 225, 250, 275, 300, 325, 350, 375, 400, 425, 450, 475, or 500 cm$^3$/m$^2$·day (as measured in accordance with AS™ D3985).

In some embodiments, the containers reduce the amount of ambient light that reaches said inoculant composition by about 5, 10, 15, 20, 25, 30, 35, 40, 45, 50, 55, 60, 65, 70, 75, 80, 85, 90, 95 or 100% when sealed.

In some embodiments, the containers reduce the amount of ambient moisture that reaches said inoculant composition by about 5, 10, 15, 20, 25, 30, 35, 40, 45, 50, 55, 60, 65, 70, 75, 80, 85, 90, 95 or 100% when sealed.

In some embodiments, the containers reduce the amount of ambient oxygen that reaches said inoculant composition by about 5, 10, 15, 20, 25, 30, 35, 40, 45, 50, 55, 60, 65, 70, 75, 80, 85, 90, 95 or 100% when sealed.

The present disclosure extends to methods and uses for fungal strains and inoculant compositions of the present disclosure.

In some embodiments, methods and uses of the present disclosure comprise, consist essentially of or consist of applying one or more fungal strains (or inoculant compositions) of the present disclosure to a medium comprising one or more insoluble forms of phosphorous (e.g., insoluble phosphates) in an amount/concentration effective to increase the amount/concentration of soluble phosphate in said medium. According to some embodiments, the fungal strain(s)/inoculant composition(s) is/are applied in an amount/concentration effective to increase the amount/concentration of soluble phosphate by at least about 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control medium (e.g., an identical medium treated with a control composition that is identical to the inoculant composition of the present disclosure except that it lacks one or more of the fungal strains of the present disclosure found in the inoculant composition of the present disclosure).

In some embodiments, methods and uses of the present disclosure comprise, consist essentially of or consist of introducing one or more fungal strains (or inoculant compositions) of the present disclosure into a medium comprising one or more insoluble forms of phosphorous (e.g., insoluble phosphates) in an amount/concentration effective to increase the amount/concentration of soluble phosphate in said medium. According to some embodiments, the fungal strain(s)/inoculant composition(s) is/are introduced in an amount/concentration effective to increase the amount/concentration of soluble phosphate by at least about 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control medium (e.g., an identical medium treated with a control composition that is identical to the inoculant composition of the present disclosure except that it lacks one or more of the fungal strains of the present disclosure found in the inoculant composition of the present disclosure).

In some embodiments, methods and uses of the present disclosure comprise, consist essentially of or consist of applying one or more fungal strains (or inoculant compositions) of the present disclosure to a medium comprising one or more insoluble forms of phosphorous (e.g., insoluble phosphates) in an amount/concentration effective to decrease the amount/concentration of phosphorous that must be added to the plant growth medium in order to achieve a desired outcome. According to some embodiments, the fungal strain(s)/inoculant composition(s) is/are applied in an amount/concentration effective to decrease the amount/concentration of phosphorous that must be added to the plant growth medium in order to achieve a desired outcome by at least about 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control medium (e.g., an identical medium treated with a control composition that is identical to the inoculant composition of the present disclosure except that it lacks one or more of the fungal strains of the present disclosure found in the inoculant composition of the present disclosure).

In some embodiments, methods and uses of the present disclosure comprise, consist essentially of or consist of introducing one or more fungal strains (or inoculant compositions) of the present disclosure into a medium comprising one or more insoluble forms of phosphorous (e.g., insoluble phosphates) in an amount/concentration effective to decrease the amount/concentration of phosphorous that must be added to the plant growth medium in order to achieve a desired outcome. According to some embodiments, the fungal strain(s)/inoculant composition(s) is/are introduced in an amount/concentration effective to decrease the amount/concentration of phosphorous that must be added to the plant growth medium in order to achieve a desired outcome by at least about 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control medium (e.g., an identical medium treated with a control composition that is identical to the inoculant composition of the present disclosure except that it lacks one or more of the fungal strains of the present disclosure found in the inoculant composition of the present disclosure).

Those skilled in the art will understand how to select an effective method of application and amount/concentration using routine dose-response experiments. In some embodiments, the fungal cells/spores are applied/introduced (in) to the medium at a rate of about $1 \times 10^1$ to about $1 \times 10^{20}$ cfu per kilogram of media, optionally about/at least $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, $1 \times 10^{15}$ fungal cells/spores per kilogram of media. According to some embodiments, an average of about/at least $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$ cfu of *P. bilaiae* NRRL B-67154, *P. bilaiae* NRRL B-67155, *P. bilaiae* NRRL B-67156, *P. bilaiae* NRRL B-67157, *P. bilaiae* NRRL B-67158, and/or *P. bilaiae* NRRL B-67159 are applied/introduced (in) to each kilogram of media.

Particular embodiments of the present disclosure are described in the following numbered paragraphs:

1. The isolated strain of *Penicillium bilaiae* having the deposit accession number NRRL 67154 (*P. bilaiae* NRRL B-67154).
2. The isolated strain of *Penicillium bilaiae* having the deposit accession number NRRL 67155 (*P. bilaiae* NRRL B-67155).
3. The isolated strain of *Penicillium bilaiae* having the deposit accession number NRRL 67156 (*P. bilaiae* NRRL B-67156).
4. The isolated strain of *Penicillium bilaiae* having the deposit accession number NRRL 67157 (*P. bilaiae* NRRL B-67157).
5. The isolated strain of *Penicillium bilaiae* having the deposit accession number NRRL 67158 (*P. bilaiae* NRRL B-67158).
6. The isolated strain of *Penicillium bilaiae* having the deposit accession number NRRL 67159 (*P. bilaiae* NRRL B-67159).
7. The progeny of any one or more of the isolated strains of paragraphs 1-6.
8. A modified microbial strain derived from the isolated strain of any one of paragraphs 1-6 or the progeny of paragraph 7.
9. A biologically pure culture of the isolated strain of any one of paragraphs 1-6.
10. A biologically pure culture of the progeny of paragraph 7.
11. A biologically pure culture of the modified microbial strain of paragraph 8.
12. An inoculant composition comprising, consisting essentially of or consisting of a carrier and one or more fungal strains, said one or more fungal strains comprising, consisting essentially of or consisting of:
   the isolated strain of any one paragraphs 1-6;
   the progeny of paragraph 7; and/or
   the modified microbial strain of paragraph 8.
13. The inoculant composition of paragraph 12, wherein said one or more fungal strains is present in said inoculant composition in an amount/concentration ranging from about $1 \times 10^1$ to about $1 \times 10^{15}$ colony-forming units of said one or more fungal strains per gram and/or milliliter of said inoculant composition, optionally $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$ or more colony-forming units per gram and/or milliliter of said inoculant composition.
14. The inoculant composition of paragraph 12, wherein said one or more fungal strains comprises:

about $1\times10^1$ to about $1\times10^{12}$ colony-forming units *P. bilaiae* NRRL B-67154 per gram and/or millileter of said inoculant composition, optionally $1\times10^4$, $1\times10^5$, $1\times10^6$, $1\times10^7$, $1\times10^8$, $1\times10^9$, $1\times10^{10}$ or more colony-forming units per gram and/or millileter of said inoculant composition;

about $1\times10^1$ to about $1\times10^{12}$ colony-forming units of *P. bilaiae* NRRL B-67155 per gram and/or millileter of said inoculant composition, optionally $1\times10^4$, $1\times10^5$, $1\times10^6$, $1\times10^7$, $1\times10^8$, $1\times10^9$, $1\times10^{10}$ or more colony-forming units per gram and/or millileter of said inoculant composition;

about $1\times10^1$ to about $1\times10^{12}$ colony-forming units of *P. bilaiae* NRRL B-67156 per gram and/or millileter of said inoculant composition, optionally $1\times10^4$, $1\times10^5$, $1\times10^6$, $1\times10^7$, $1\times10^8$, $1\times10^9$, $1\times10^{10}$ or more colony-forming units per gram and/or millileter of said inoculant composition;

about $1\times10^1$ to about $1\times10^{12}$ colony-forming units of *P. bilaiae* NRRL B-67157 per gram and/or millileter of said inoculant composition, optionally $1\times10^4$, $1\times10^5$, $1\times10^6$, $1\times10^7$, $1\times10^8$, $1\times10^9$, $1\times10^{10}$ or more colony-forming units per gram and/or millileter of said inoculant composition;

about $1\times10^1$ to about $1\times10^{12}$ colony-forming units of *P. bilaiae* NRRL B-67158 per gram and/or millileter of said inoculant composition, optionally $1\times10^4$, $1\times10^5$, $1\times10^6$, $1\times10^7$, $1\times10^8$, $1\times10^9$, $1\times10^{10}$ or more colony-forming units per gram and/or millileter of said inoculant composition; and/or about $1\times10^1$ to about $1\times10^{12}$ colony-forming units of *P. bilaiae* NRRL B-67159 per gram and/or millileter of said inoculant composition, optionally $1\times10^4$, $1\times10^5$, $1\times10^6$, $1\times10^7$, $1\times10^8$, $1\times10^9$, $1\times10^{10}$ or more colony-forming units per gram and/or millileter of said inoculant composition.

15. The inoculant composition of paragraph 12, wherein said one or more fungal strains is present in said inoculant composition in an amount effective to increase the amount/concentration of soluble phosphate in a medium that comprises insoluble phosphate, when the inoculant composition is introduced into said medium.

16. The inoculant composition of any one paragraphs 12-15, said composition further comprising one or more stabilizing compounds.

17. The inoculant composition of paragraph 16, said one or more stabilizing compounds comprising, consisting essentially of or consisting of:

one or more monosaccharides, optionally arabinose, fructose and/or glucose; one or more disaccharides, optionally maltose, sucrose and/or trehalose;

one or more maltodextrins, optionally one or more maltodextrins (e.g., one or more maltodextrins (each and/or collectively) having a DEV value of about 15 to about 20;

one or more sugar alcohols, optionally arabitol, mannitol, sorbitol and/or xylitol;

one or more humic acids, optionally potassium humate and/or sodium humate;

one or more hygroscopic polymers, optionally one or more albumins, alginates, celluloses, gums (e.g., cellulose gum, guar gum, gum arabic, gum combretum, xantham gum), methyl celluloses, nylons, pectins, polyacrylic acids, polycarbonates, polyethylene glycols (PEG), polyethylenimines (PEI), polylactides, polymethylacrylates (PMA), polyurethanes, polyvinyl alcohols (PVA), polyvinylpyrrolidones (PVP), propylene glycols, sodium carboxymethyl celluloses and/or starches;

one or more oxidation control components, optionally one or more antioxidants (e.g., ascorbic acid, ascorbyl palmitate, ascorbyl stearate, calcium ascorbate, one or more carotenoids, lipoic acid, one or more phenolic compounds (e.g., one or more flavonoids, flavones and/or flavonols), potassium ascorbate, sodium ascorbate, one or more thiols (e.g., glutathione, lipoic acid and/or N-acetyl cysteine), one or more tocopherols, one or more tocotrienols, ubiquinone and/or uric acid) and/or one or more oxygen scavengers, optionally ascorbic acid and/or sodium hydrogen carbonate; and/or one or more UV protectants, optionally one or more lignosulfites.

18. The inoculant composition of any one paragraphs 16-17, said one or more stabilizing compounds comprising about 0.0001 to about 10% (by weight) of said composition, optionally about 2 to about 6% (by weight) of said composition, optionally about 0.0005, 0.001, 0.002, 0.003, 0.004, 0.005, 0.0075, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 1, 1.5, 2, 2.5, 3, 3.5, 4, 4.5, 5, 5.5, 6, 7, 7.5, 8, 8.5, 9, 9.5 or 10% (by weight) of said composition.

19. The inoculant composition of any one of paragraphs 16-18, wherein said one or more stabilizing compounds is/are present in an amount/concentration sufficient to ensure said one or more fungal strains remains viable in inoculant compositions of the present disclosure following:

storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

desiccation by about 5, 10, 15, 20, 25, 30, 35, 40, 45, 50, 55, 60, 65, 70, 75, 80, 85, 90, 95% or more;

desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

application;

application and desiccation by about 5, 10, 15, 20, 25, 30, 35, 40, 45, 50, 55, 60, 65, 70, 75, 80, 85, 90, 95% or more; and/or application and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more.

20. The inoculant composition of any one of paragraphs 16-18, wherein said one or more stabilizing compounds is/are present in an amount/concentration sufficient to ensure at least 0.01, 0.05, 0.1, 0.5, 1, 2, 3, 4, 5, 10, 15, 20, 25, 30, 35, 40, 45, 50, 55, 60, 65, 70, 75, 80, 85, 90, 95% of said one or more fungal strains remains viable following:

storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

desiccation by about 5, 10, 15, 20, 25, 30, 35, 40, 45, 50, 55, 60, 65, 70, 75, 80, 85, 90, 95% or more;

desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

application;

application and desiccation by about 5, 10, 15, 20, 25, 30, 35, 40, 45, 50, 55, 60, 65, 70, 75, 80, 85, 90, 95% or more; and/or application and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more.

21. The inoculant composition of any one of paragraphs 16-18, wherein said one or more stabilizing compounds is/are present in an amount/concentration sufficient to ensure at least $1 \times 10^1$, $1 \times 10^2$, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$ or more colony-forming units of said one or more fungal strains per gram and/or milliliter of inoculant composition remain viable following:

storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

desiccation by about 5, 10, 15, 20, 25, 30, 35, 40, 45, 50, 55, 60, 65, 70, 75, 80, 85, 90, 95% or more;

desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

application;

application and desiccation by about 5, 10, 15, 20, 25, 30, 35, 40, 45, 50, 55, 60, 65, 70, 75, 80, 85, 90, 95% or more; and/or application and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more.

22. The inoculant composition of any one of paragraphs 12-21, said composition further comprising one or more additional microorganisms.

23. The inoculant composition of paragraph 22, said one or more additional microorganisms comprising, consisting essentially of or consisting of *Azospirillum brasilense* INTA Az-39, *Bacillus amyloliquefaciens* D747, *Bacillus amyloliquefaciens* NRRL B-50349, *Bacillus amyloliquefaciens* TJ1000, *Bacillus amyloliquefaciens* FZB24, *Bacillus amyloliquefaciens* FZB42, *Bacillus amyloliquefaciens* IN937a, *Bacillus amyloliquefaciens* IT-45, *Bacillus amyloliquefaciens* TJ1000, *Bacillus amyloliquefaciens* MBI600, *Bacillus amyloliquefaciens* BS27 (deposited as NRRL B-5015), *Bacillus amyloliquefaciens* BS2084 (deposited as NRRL B-50013), *Bacillus amyloliquefaciens* 15AP4 (deposited as ATCC PTA-6507), *Bacillus amyloliquefaciens* 3AP4 (deposited as ATCC PTA-6506), *Bacillus amyloliquefaciens* LSSA01 (deposited as NRRL B-50104), *Bacillus amyloliquefaciens* ABP278 (deposited as NRRL B-50634), *Bacillus amyloliquefaciens* 1013 (deposited as NRRL B-50509), *Bacillus amyloliquefaciens* 918 (deposited as NRRL B-50508), *Bacillus amyloliquefaciens* 22CP1 (deposited as ATCC PTA-6508) and *Bacillus amyloliquefaciens* BS18 (deposited as NRRL B-50633), *Bacillus cereus* 1-1562, *Bacillus firmus* 1-1582, *Bacillus licheniformis* BA842 (deposited as NRRL B-50516), *Bacillus licheniformis* BL21 (deposited as NRRL B-50134), *Bacillus mycoides* NRRL B-21664, *Bacillus pumilus* NRRL B-21662, *Bacillus pumilus* NRRL B-30087, *Bacillus pumilus* ATCC 55608, *Bacillus pumilus* ATCC 55609, *Bacillus pumilus* GB34, *Bacillus pumilus* KFP9F, *Bacillus pumilus* QST 2808, *Bacillus subtilis* ATCC 55078, *Bacillus subtilis* ATCC 55079, *Bacillus subtilis* MBI 600, *Bacillus subtilis* NRRL B-21661, *Bacillus subtilis* NRRL B-21665, *Bacillus subtilis* CX-9060, *Bacillus subtilis* GB03, *Bacillus subtilis* GB07, *Bacillus subtilis* QST-713, *Bacillus subtilis* FZB24, *Bacillus subtilis* D747, *Bacillus subtilis* 3BP5 (deposited as NRRL B-50510), *Bacillus thuringiensis* ATCC 13367, *Bacillus thuringiensis* GC-91, *Bacillus thuringiensis* NRRL B-21619, *Bacillus thuringiensis* ABTS-1857, *Bacillus thuringiensis* SAN 401 I, *Bacillus thuringiensis* ABG-6305, *Bacillus thuringiensis* ABG-6346, *Bacillus thuringiensis* AM65-52, *Bacillus thuringiensis* SA-12, *Bacillus thuringiensis* SB4, *Bacillus thuringiensis* ABTS-351, *Bacillus thuringiensis* HD-1, *Bacillus thuringiensis* EG 2348, *Bacillus thuringiensis* EG 7826, *Bacillus thuringiensis* EG 7841, *Bacillus thuringiensis* DSM 2803, *Bacillus thuringiensis* NB-125, *Bacillus thuringiensis* NB-176, BRADY, *Pseudomonas jessenii* PS06, *Rhizobium leguminosarum* S012A-2 (IDAC 080305-01), *Sinohizobium fredii* CCBAU114 and/or *Sinohizobium fredii* USDA 205, and/or *Yersinia entomophaga* O82KB8.

24. The inoculant composition of paragraph 23, said one or more additional microorganisms comprising, consisting essentially of or consisting of *Gliocladium virens* ATCC 52045, *Gliocladium virens* GL-21, *Glomus intraradices* RTI-801, *Metarhizium anisopliae* F52, PENI, *Trichoderma asperellum* SKT-1, *Trichoderma asperellum* ICC 012, *Trichoderma afroviride* LC52, *Trichoderma afroviride* CNCM 1-1237, *Trichoderma fertile* JM41R, *Trichoderma gamsii* ICC 080, *Trichoderma hamatum* ATCC 52198, *Trichoderma harzianum* ATCC 52445, *Trichoderma harzianum KRL-AG2, *Trichoderma harzianum* T-22, *Trichoderma harzianum* TH-35, *Trichoderma harzianum* T-39, *Trichoderma harzianum* ICC012, *Trichoderma reesi* ATCC 28217, *Trichoderma virens* ATCC 58678, *Trichoderma virens* G1-3, *Trichoderma virens* GL-21, *Trichoderma virens* G-41, *Trichoderma viridae* ATCC 52440, *Trichoderma viridae* ICC080, and/or *Trichoderma viridae* TV1.

25. The inoculant composition of paragraph 23, said one or more additional microorganisms comprising, consisting essentially of or consisting of one or more biopesticides, optionally one or more acaricidal, insecticidal and/or nematicidal microorganisms and one or more fungicidal microorganisms.

26. The inoculant composition of any one of claims 22-25, said composition comprising about $1 \times 10^3$ to about $1 \times 10^{12}$ colony-forming units (cfu) of said one or more additional microorganisms per gram and/or milliliter of inoculant composition, optionally about/at least $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, or $1 \times 10^{12}$ cfu of said one or more additional microorganisms per gram and/or milliliter of inoculant composition.

27. The inoculant composition of any one paragraphs 12-26, wherein said composition is non-aqueous.

28. The inoculant composition of any one paragraphs 12-26, wherein said composition is aqueous.

29. The inoculant composition of any one paragraphs 12-26, wherein said composition comprises less than 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.25, 1.5, 1.75, 2, 2.25, 2.5, 2.75, 3, 3.25, 3.5, 3.75, 4, 4.25, 4.5, 4.75 or 5% water (by weight, based upon the total weight of the composition).

30. The inoculant composition of any one paragraphs 12-26, wherein said composition is an amorphous liquid.

31. The inoculant composition of any one paragraphs 12-26, wherein said composition is an amorphous solid.

32. The inoculant composition of any one paragraphs 12-26, wherein said composition is a freeze-, spray- or spray-freeze-dried composition, optionally a freeze-, spray- or spray-freeze-dried powder.

33. A kit, comprising:
the inoculant composition of any one of paragraphs any one of paragraphs 12-32; and
a container housing said inoculant composition.

34. The kit of claim 33, said container reducing the amount of ambient light that reaches said inoculant composition by about 5, 10, 15, 20, 25, 30, 35, 40, 45, 50, 55, 60, 65, 70, 75, 80, 85, 90, 95 or 100% when sealed.

35. The kit of any one of paragraphs 33-34, said container reducing the amount of ambient oxygen that reaches said inoculant composition by about 5, 10, 15, 20, 25, 30, 35, 40, 45, 50, 55, 60, 65, 70, 75, 80, 85, 90, 95 or 100% when sealed.

36. The kit of any one of paragraphs 33-35, said container comprising, consisting essentially of, or consisting of a material having light permeability of less than about 1, 2, 3, 4, 5, 6, 7, 8, 9, 10, 15, 20, 25, 30, 35, 40, 45, 50, 55, 60, 65, 70 or 75%.

37. The kit of any one of paragraphs 33-36, said container comprising, consisting essentially of, or consisting of a material having an oxygen transmission rate of less than about 5, 10, 15, 20, 25, 30, 35, 40, 45, 50, 60, 70, 80, 90, 100, 125, 150, 175, 200, 225, 250, 275, 300, 325, 350, 375, 400, 425, 450, 475, or 500 cm$^3$/m$^2$·day (as measured in accordance with ASTM D3985).

38. The kit of any one of paragraphs 33-37, said kit furthering comprising one or more oxygen-absorbing compound, optionally activated carbon, iron powder, sodium chloride, ferrous carbonate, one or more metal halide catalysts and/or sodium hydrogen carbonate.

39. Use of *P. bilaiae* NRRL 67154, *P. bilaiae* NRRL 67155, *P. bilaiae* NRRL 67156, *P. bilaiae* NRRL 67157, *P. bilaiae* NRRL 67158, and/or *P. bilaiae* NRRL 67159 to solubilize phosphate in a medium that comprises one or more insoluble phosphates.

40. A method, comprising, consisting essentially of, or consisting of: applying the isolated strain of any one of paragraphs 1-6, the progeny of paragraph 7, the modified microbial strain of paragraph 8, the biologically pure culture of any one of paragraphs 9-11 and/or the inoculant composition of any one of paragraphs 12-32 to a phosphate-comprising medium in an amount/concentration effective to increase the amount/concentration of soluble phosphate in said medium.

41. A method, comprising, consisting essentially of, or consisting of:
introducing the isolated strain of any one of paragraphs 1-6, the progeny of paragraph 7, the modified microbial strain of paragraph 8, the biologically pure culture of any one of paragraphs 9-11 and/or the inoculant composition of any one of paragraphs 12-32 into a phosphate-comprising medium in an amount/concentration effective to increase the amount/concentration of soluble phosphate in said medium.

Deposit of Biological Material

Each of the isolated *Penicillium bilaiae* strains provided by the present disclosure-NRRL 67154, NRRL 67155, NRRL 67156, NRRL 67157, NRRL 67158 and NRRL 67159—was isolated from a soil sample collected in Canada and deposited on Dec. 2, 2015 under the terms of the Budapest Treaty on the International Recognition of the Deposit of Microorganisms for the Purposes of Patent Procedure at the Agricultural Research Service Culture Collection, 1815 North University Street, Peoria, Ill. 61604, U.S.A.

Each strain was deposited under conditions that assure access to the culture will be available during the pendency of this patent application to one determined by the Commissioner of Patents and Trademarks to be entitled thereto under 37 C.F.R. § 1.14 and 35 U.S.C. § 122. Each deposit represents a pure culture of the deposited strain. Each deposit is available as required by foreign patent laws in countries wherein counterparts of the subject application or its progeny are filed. However, it should be understood that the availability of a deposit does not constitute a license to practice the subject invention in derogation of patent rights granted by governmental action.

EXAMPLES

The following examples are not intended to be a detailed catalogue of all the different ways in which the present disclosure may be implemented or of all the features that may be added to the present disclosure. Subjects skilled in the art will appreciate that numerous variations and additions to the various embodiments may be made without departing from the present disclosure. Hence, the following descriptions are intended to illustrate some particular embodiments of the invention and not to exhaustively specify all permutations, combinations and variations thereof.

Example 1

Isolation of Phosphate-Solubilizing Microorganisms 128 soil samples were serially diluted and plated onto precipitated phosphate rose Bengal agar plates. Colonies that produced clearing zones were isolated and used to establish pure cultures of the microorganism(s) contained therein.

Example 2

Identification of Improved Phosphate-Solubilizing Microorganisms

Phosphate solubilization assays of 118 isolates from Example 1 were carried out in 96-well microbioreactor plates (EnzyScreen, Netherlands) in 1.5 ml of nitrate free minimal salts medium (0.1 g/l NaCl; 0.4 g/l $NH_4Cl$; 0.1 g/l $CaCl_2*H_2O$; 1.0 g/l $MgSO_4*7H_2O$; 10.0 g/l sucrose; 5.41 g/l hydroxyapatite). The plates were inoculated from glycerol spore suspension stock plates stored at 80° C. using a 96-pin cryo-replicator that was heat sterilized and cooled before transfer. Plates were grown at room temperature (20-25° C.) and 300 rpm for 14 days. After 14 days, the plate was centrifuged for 5 minutes at 5100 rpm and 1 ml of the supernatant was transferred to a 96-well filter plate (Acro-Prep Advance 96 multi-well filter plate, 1 µm glass fibre, Pall Life Sciences #8231). The filter plate was placed over a 2 ml receiver plate (Whatman Uniplate 96well round bottom, Whatman #7701-5200) and samples were filtered under vacuum using a multi-well plate vacuum manifold (Pall Life Sciences #5017). The filtered supernatants were diluted 100× with sterile water and soluble phosphate was measured using a plate reading spectrophotometer (Biotek, Winooski, Vt.) with the BioVision Phosphate Colorimetric Assay Kit (BioVision Research Products, Mountain View, Calif.) and accompanying instructions. Each isolate was grown and tested for phosphate solubilization in triplicate and the averages and standard deviations were calculated. Six of the isolates exhibited enhanced phosphate-solubilization as compared to *Penicillium bilaiae* ATCC-20851. Those six isolates were identified as *Penicillium bilaiae* and deposited under the terms of the Budapest Treaty and given the accession numbers NRRL 67154, NRRL 67155, NRRL 67156, NRRL 67157, NRRL 67158 and NRRL 67159. Table 1.

TABLE 1

Results of Phosphate Solubilaztion Assay

| Strain | Increase in solubilized phosphate (as compared to ATCC-20851) |
|---|---|
| NRRL 67154 | 30.86% increase |
| NRRL 67155 | 28.16% increase |
| NRRL 67156 | 10.35% increase |
| NRRL 67157 | 10.56% increase |
| NRRL 67158 | 15.65% increase |
| NRRL 67159 | 16.5% increase |

APPENDIX A

Acinetobacter, Actinomycetes, Aegerita, Agrobacterium (e.g., *A. radiobacter* strains such as K1026 and K84), Akanthomyces, Alcaligenes, Alternaria, Aminobacter (e.g., *A. aganoensis, A. aminovorans, A. anthyllidis, A. ciceronei, A. lissarensis, A. niigataensis*), Ampelomyces (e.g., *A. quisqualis* strains such as M-10), Anabaena (e.g., *A. aequalis, A. affinis, A. angstumalis angstumalis, A. angstumalis marchita, A. aphanizomendoides, A. azollae, A. bornetiana, A. catenula, A. cedrorum, A. circinalis, A. confervoides, A. consfricta, A. cyanobacterium, A. cycadeae, A. cylindrica, A. echinispora, A. felisii, A. flos-aquae flos-aquae, A. flos-aquae minor, A. flos-aquae freleasei, A. helicoidea, A. inaequalis, A. lapponica, A. laxa, A. lemmermannii, A. levanderi, A. limnetica, A. macrospora macrospora, A. macrospora robusta, A. monticulosa, A. nostoc, A. ascillarioides, A. planctonica, A. raciborski, A. scheremetievi, A. sphaerica, A. spiroides crassa, A. spiroides sprroides, A. subcylindrica, A. torulosa, A. unispora, A. variabilis, A. verrucosa, A. viguieri, A. wisconsinense, A. zierlingii*), Arthrobacter, Arthrobotrys (e.g., *A. aggregata, A. alaskana, A. ameropora, A. anomala, A. apscheronica, A. arthrobotryoides, A. azerbaijanica, A. bakunika, A. botryospora, A. brochopaga, A. chazarica, A. chilensis, A. cladodes, A. calvispora, A. compacta, A. conoides, A. consfringens, A. cylindrospora, A. dactyloides, A. deflectans, A. dendroides, A. doliiformis, A. drechsleri, A. elegans, A. ellipsospora, A. entomopaga, A. ferox, A. foliicola, A. fruticulosa, A. globospora, A. hatospora, A. hertziana, A. indica, A. irregularis, A. javanica, A. kirghizica, A. longa, A. longiphora, A. longiramulifera, A. longispora, A. mangrovispora, A. megaspora, A. microscaphoides, A. microspora, A. multisecundaria, A. musiformis, A. nematopaga, A. nonseptata, A. oligospora, A. oudemansii, A. oviformis, A. perpasta, A. polycephala, A. pseudoclavata, A. pyriformis, A. recta, A. robusta, A. rosea, A. scaphoides, A. sclerohypha, A. shahriari, A. shizishanna, A. sinensis, A. soprunovii, A. stilbacea, A. straminicola, A. superba, A. tabrizica, A. venusta, A. vermicola, A. yunnanensis*), Aschersonia, Ascophaera, Aspergillus (e.g., *A. flavus* strains such as NRRL 21882, *A. parasiticus*), Aulosira (e.g., *A. aenigmatica, A. africana, A. bohemensis, A. bombayensis, A. confluens, A. fertilissima, A. fertilissma* var. *tenius, A. fritschii, A. godoyana, A. implexa, A. laxa, A. plantonica, A. prolifica, A. pseuodoramosa, A. schauinslandii, A. striata, A. terrestris, A. thermalis*), Aureobacterium, Aureobasidium (e.g., *A. pullulans* strains such as DSM 14940 and DSM 14941), Azobacter, Azorhizobium (e.g., *A. caulinodans, A. doebereinerae, A. oxalatiphilum*), Azospirillum (e.g., *A. amazonense* strains such as BR 11140 (SpY2T), *A. brasilense* strains such as INTA Az-39, AZ39, XOH, BR 11002, BR 11005, Ab-V5 and Ab-V6, *A. canadense, A. doebereinerae, A. formosense, A. halopraeferans, A. irakense, A. largimobile, A. lipoferum* strains such as BR 11646, *A. melinis, A. oryzae, A. picis, A. rugosum, A. thiophilum, A. zeae*), Azotobacter (e.g., *A. agilis, A. armeniacus,* A. sp. AR, *A. beijerinckii, A. chroococcum,* A. DCU26, A. FAB, *A. nigricans, A. paspali, A. salinesfris, A. tropicalis, A. vinelandii*), Bacillus (e.g., *B. amyloliquefaciens* strains such as D747, NRRL B-50349, TJ1000 (also known as 1BE, isolate ATCC BAA-390), FZB24, FZB42, IN937a, IT-45, TJ1000, MBI600, BS27 (deposited as NRRL B-5015), BS2084 (deposited as NRRL B-50013), 15AP4 (deposited as ATCC PTA-6507), 3AP4 (deposited as ATCC PTA-6506), LSSA01 (deposited as NRRL B-50104), ABP278 (deposited as NRRL B-50634), 1013 (deposited as NRRL B-50509), 918 (deposited as NRRL B-50508), 22CP1 (deposited as ATCC PTA-6508) and BS18 (deposited as NRRL B-50633), *B. cereus* strains such as 1-1562, *B. firmus* strains such as 1-1582, *B. laevolacticus, B. lichenformis* strains such as BA842 (deposited as NRRL B-50516) and BL21 (deposited as NRRL B-50134), *B. macerns, B. firmus, B. mycoides* strains such as NRRL B-21664, *B. pasteurii, B. pumilus* strains such as NRRL B-21662, NRRL B-30087, ATCC 55608, ATCC 55609, GB34, KFP9F and QST 2808, *B. sphaericus*, *B. subtilis* strains such as ATCC 55078, ATCC 55079, MBI 600, NRRL B-21661, NRRL B-21665, CX-9060, GB03, GB07, QST 713, FZB24, D747 and 3BP5 (deposited as NRRL B-50510), *B. thuringiensis* strains such as ATCC 13367, GC-91, NRRL B-21619, ABTS-1857, SAN 401 I, ABG-6305, ABG-6346, AM65-52, SA-12, SB4, ABTS-351, HD-1, EG 2348, EG 7826, EG 7841, DSM 2803, NB-125 and NB-176), *Beijerinckia*, *Beauveria* (e.g., *B. bassiana* strains such as ATCC 26851, ATCC 48023, ATCC 48585, ATCC 74040, ATCC-74250, DSM 12256 and PPRI 5339), *Beijerinckia*, *Blastodendrion*, *Bosea* (e.g., *B. eneae*, *B. lathyri*, *B. lupini*, *B. massiliensis*, *B. minatitlanensis*, *B. robiniae*, *B. thiooxidans*, *B. vestrisii*), *Bradyrhizobium* (e.g., *B. arachidis*, *B. bete*, *B. canariense*, *B. cytisi*, *B. daqingense*, *B. denifrificans*, *B. diazoefficiens*, *B. elkanii* strains such as SEMIA 501, SEMIA 587 and SEMIA 5019, *B. ganzhouense*, *B. huanghuauhaiense*, *B. icense*, *B. ingae*, *B. iriomotense*, *B. japonicum* strains such as NRRL B-50586 (also deposited as NRRL B-59565), NRRL B-50587 (also deposited as NRRL B-59566), NRRL B-50588 (also deposited as NRRL B-59567), NRRL B-50589 (also deposited as NRRL B-59568), NRRL B-50590 (also deposited as NRRL B-59569), NRRL B-50591 (also deposited as NRRL B-59570), NRRL B-50592 (also deposited as NRRL B-59571), NRRL B-50593 (also deposited as NRRL B-59572), NRRL B-50594 (also deposited as NRRL B-50493), NRRL B-50608, NRRL B-50609, NRRL B-50610, NRRL B-50611, NRRL B-50612, NRRL B-50726, NRRL B-50727, NRRL B-50728, NRRL B-50729, NRRL B-50730, SEMIA 566, SEMIA 5079, SEMIA 5080, USDA 6, USDA 110, USDA 122, USDA 123, USDA 127, USDA 129 and USDA 532C, *B. jicamae*, *B. lablabi*, *B. liaoningense*, *B. manausense*, *B. neofropicale*, *B. oligofrophicum*, *B. ottawaense*, *B. pachyrhizi*, *B. paxllaeri*, *B. retamae*, *B. rifense*, *B. valentinum*, *B. yuanmingense*), *Burkholderia* (e.g., *B. acidipaludis*, *B. ambifaria*, *B. andropogonis*, *B. anthina*, *B. arboris*, *B. bannensis*, *B. bryophila*, *B. caledonica*, *B. caribensis*, *B. caryophylli*, *B. cenocepacua*, *B. choica*, *B. cocovenenans*, *B. contaminans*, *B. denitrificans*, *B. diazofrophica*, *B. diffusa*, *B. dilworthii*, *B. dolosa*, *B. eburnea*, *B. endofungorum*, *B. ferrariae*, *B. fungorum*, *B. ginsengisoli*, *B. gladioli*, *B. glathei*, *B. glumae*, *B. graminis*, *B. grimmiae*, *B. heleia*, *B. hospital*, *B. humi*, *B. kururiensis*, *B. lata*, *B. latens*, *B. mallei*, *B. megapolitana*, *B. metallica*, *B. mimosarum*, *B. multivorans*, *B. nodosa*, *B. norimbergensis*, *B. oklahomensis*, *B. phenazinium*, *B. phenolirupfrix*, *B. phymatum*, *B. phytofirmans*, *B. pickettii*, *B. plantarii*, *B. pseudomallei*, *B. pseudomultivorans*, *B. pyrrocinia*, *B. rhizoxinica*, *B. rhynchosiae*, *B. sabiae*, *B. sacchari*, *B. sartisoli*, *B. sediminicola*, *B. seminalis*, *B. silvatlantica*, *B. singaporensis*, *B. soli*, *B. sordidcola*, B. sp. strains such as A396, *B. sprentiae*, *B. stabilis*, *B. symbiotica*, *B. telluris*, *B. terrae*, *B. terrestris*, *B. terricola*, *B. thailandensis*, *B. tropica*, *B. tuberum*, *B. ubonensis*, *B. udeis*, *B. unamae*, *B. vandii*, *B. vietnamiensis*, *B. xenovorans*, *B. zhejiangensis*), *Brevibacillus*, *Burkholderia* (e.g., B. sp. A396 nov. rinojensis NRRL B-50319), *Calonectria*, *Candida* (e.g., *C. oleophila* such 1-182, *C. saitoana*), *Candidatus* (e.g., *C. Burkholderia calva*, *C. Burkholderia crenata*, *C. Burkholderia hispidae*, *C. Burkholderia kirkii*, *C. Burkholderia mamillata*, *C. Burkholderia nigropunctata*, *C. Burkholderia rigidae*, *C. Burkholderia schumannianae*, *C. Burkholderia verschuerenii*, *C. Burkholderia virens*, *C. Phytoplasma allocasuarinae*, *C. Phytoplasma americanum*, *C. Phytoplasma asteris*, *C. Phytoplasma aurantifolia*, *C. Phytoplasma australiense*, *C. Phytoplasma balanitae*, *C. Phytoplasma brasiliense*, *C. Phytoplasma caricae*, *C. Phytoplasma castaneae*, *C. Phytoplasma cocosnigeriae*, *C. Phytoplasma cocostanzaniae*, *C. Phytoplasma convolvuli*, *C. Phytoplasma costaricanum*, *C. Phytoplasma cynodontis*, *C. Phytoplasma fragariae*, *C. Phytoplasma fraxini*, *C. Phytoplasma graminis*, *C. Phytoplasma japonicum*, *C. Phytoplasma luffae*, *C. Phytoplasma lycopersici*, *C. Phytoplasma malasianum*, *C. Phytoplasma mali*, *C. Phytoplasma omanense*, *C. Phytoplasma oryzae*, *C. Phytoplasma palmae*, *C. Phytoplasma palmicola*, *C. Phytoplasma phoenicium*, *C. Phytoplasma pini*, *C. Phytoplasma pruni*, *C. Phytoplasma prunorum*, *C. Phytoplasma pyri*, *C. Phytoplasma rhamni*, *C. Phytoplasma rubi*, *C. Phytoplasma solani*, *C. Phytoplasma spartii*, *C. Phytoplasma sudamericanum*, *C. Phytoplasma tamaricis*, *C. Phytoplasma trifolii*, *C. Phytoplasma ulmi*, *C. Phytoplasma vitis*, *C. Phytoplasma Chromobacterium* (e.g., *C. subtsugae* NRRL B-30655 and PRAA4-1, *C. vaccinia* strains such as NRRL B-50880, *C. violaceum*), *Chryseomonas*, *Clavibacter*, *Clonostachys* (e.g., *C. rosea f catenulata* (also referred to as *Gliocladium catenulatum*) strains such as J1446), *Clostridium*, *Coelemomyces*, *Coelomycidium*, *Colletofrichum* (e.g., *C. gloeosporioides* strains such as ATCC 52634), *Comomonas*, *Conidiobolus*, *Coniothyrium* (e.g., *C. minitans* strains such as CON/N/M91-08), *Cordyceps*, *Corynebacterium*, *Couchia*, *Cryphonecfria* (e.g., *C. parasitica*), *Cryptococcus* (e.g., *C. albidus*), *Cryptophlebia* (e.g., *C. leucofreta*), *Culicinomyces*, *Cupriavidus* (e.g., *C. alkaliphilus*, *C. basilensis*, *C. campinensis*, *C. gilardii*, *C. laharis*, *C. metallidurans*, *C. numazuensis*, *C. oxalaticus*, *C. pampae*, *C. pauculus*, *C. pinatubonensis*, *C. respiraculi*, *C. taiwanensis*), *Curtobacterium*, *Cydia* (e.g., *C. pomonella* strains such as V03 and V22), *Dactylaria* (e.g., *D. candida*), *Delftia* (e.g., *D. acidovorans* strains such as RAY209), *Desulforibtio*, *Desulfovibrio*, *Devosia* (e.g., *D. neptuniae*), *Dilophosphora* (e.g., *D. alopecuri*), *Engyodontium*, *Enterobacter*, *Entomophaga*, *Entomophthora*, *Erynia*, *Escherichia* (e.g., *E. intermedia*), *Eupenicillium*, *Exiguobacterium*, *Filariomyces*, *Filobasidiella*, *Flavobacterium* (e.g., F. H492 NRRL B-50584), *Frankia* (e.g., *F. alni*), *Fusarium* (e.g., *F. laterium*, *F. oxysporum*, *F. solani*), *Gibellula*, *Gigaspora* (e.g., *G. margarita*), *Gliocladium* (e.g., *G. virens* strains such as ATCC 52045 and GL-21), *Glomus* (e.g., *G. aggregatum*, *G. brasilianum clarum*, *G. deserticola*, *G. etunicatum*, *G. fasciculatum*, *G. infraradices* strains such as RTI-801 *G. monosporum*, *G. mosseae*), *Gluconobacter*, *Halospirulina*, *Harposporium* (e.g., *H. anguillulae*), *Hesperomyces*, *Hirsutella* (e.g., *H. minnesotensis*, *H. rhossiliensis*, *H. thomsonii* strains such as ATCC 24874), *Hydrogenophage*, *Hymenoscyphous* (e.g., *H. ericae*), *Hymenostilbe*, *Hypocrella*, *Isaria* (e.g., *I. fumosorosea* strains such as Apopka-97 (deposited as ATCC 20874)), *Klebsiella* (e.g., *K. pneumoniae*, *K. oxytoca*), *Kluyvera*, *Laccaria* (e.g., *L. bicolor*, *L. laccata*), *Lactobacillus*, *Lagenidium*, *Lecanicillium* (e.g., *L. lecanii* strains such as KV01, *L. longisporum* strains such as KV42 and KV71), *Leptolegnia*, *Lysobacter* (e.g., *L. antibioticus* strains such as 13-1 and HS124, *L. enzymogenes* strains such as 3.1T8), *Massospora*, *Meristacrum* (e.g., *M. asterospermum*), *Mesorhizobium* (e.g., *M. abyssinicae*, *M. albiziae*, *M. alhagi*, *M. amorphae*, *M. ausfralicum*, *M. camelthorni*, *M. caraganae*, *M. chacoense*, *M. ciceri*, *M. gobiense*, *M. hawassense*, *M. huakuii*, *M. loti*, *M. mediterraneum*, *M. metallidurans*, *M. muleiense*, *M. opportunistum*, *M. plurifarium*, *M. qingshengii*, *M. robiniae*, *M. sangaii*, *M. septentrionale*, *M. shangrilense*, *M. shonense*, *M. silamurunense*, *M. tamadayense*, *M. tarimense*, *M. temperatum*, *M. thiogangeticum*, *M. tianshanense*), *Metarhizium* (e.g., *M.* anisopliae (also referred to as M. brunneum, Metarrhizium anisopliae, and green muscadine) strains such as IMI 330189, FI-985, FI-1045, F52 (deposited as DSM 3884, DSM 3885, ATCC 90448, SD 170 and ARSEF 7711) and ICIPE 69), M. flavoviride strains such as ATCC 32969), Methylobacterium (e.g., M. adhaesivum, M. aerolatum, M. aminovorans, M. aquaticum, M. brachiatum, M. brachythecii, M. bullatum, M. cerastii, M. chloromethanicum, M. dankookense, M. dichloromethanicum, M. extorquens, M. fujisawaense, M. gnaphalii, M. goesingense, M. gossipiicola, M. gregans, M. haplocladii, M. hispanicum, M. iners, M. isbiliense, M. jeotgali, M. komagatae, M. longum, M. lusitanum, M. marchantiae, M. mesophilicum, M. nodulans, M. organophilum, M. oryzae, M. oxalidis, M. persicinum, M. phyllosphaerae, M. platani, M. podarium, M. populi, M. radiotolerans, M. rhodesianum, M. rhodinum, M. salsuginis, M. soli, M. suomiense, M. tardum, M. tarhaniae, M. thiocyanatum, M. thurigiense, M. trifolii, M. variabile, M. zatmanii), Metschnikowia (e.g., M. fructicola), Microbacterium (e.g., M. laevaniformans), Microdochium (e.g., M. dimerum), Microsphaeropsis (e.g., M. ochracea P130A), Microvirga (e.g., M. aerilata, M. aerophila, M. flocculans, M. guangxiensis, M. lotononidis, M. lupini, M. subterranea, M. vignae, M. zambiensis), Monacrosporium (e.g., M. cionopagum), Mucor, Muscodor (e.g., M. albus such NRRL 30547, QST 20799 and SA-13, M. roseus strains such as NRRL 30548), Mycoderma, Myiophagus, Myriangium, Myrothecium (e.g., M. verrucaria), Nectria, Nematoctonus (e.g., N. geogenius, N. leiosporus), Neozygites, Nomuraea (e.g., N. rileyi strains such as SA86101, GU87401, SR86151, CG128 and VA9101), Nostoc (e.g., N. azollae, N. caeruleum, N. carneum, N. comminutum, N. commune, N. ellipsosporum, N. flagelliforme, N. linckia, N. longstaffi, N. microscopicum, N. muscorum, N. paludosum, N. pruniforme, N. punctifrome, N. sphaericum, N. sphaeroides, N. spongiaeforme, N. verrucosum), Ochrobactrum (e.g., O. anthropi, O. cicero, O. cytisi, O. daejeonense, O. gallinifaecis, O. grigonense, O. guangzhouense, O. haematophilum, O. intermedium, O. lupini, O. oryzae, O. pectoris, O. pituitosum, O. pseudointermedium, O. pseudogrignonense, O. rhizosphaerae, O. thiophenivorans, O. tritici), Oidiodendron, Paecilomyces (e.g., P. fumosoroseus strains such as FE991 and FE 9901, P. lilacinus strains such as 251, DSM 15169 and BCP2), Paenibacillus (e.g., P. alvei strains such as NAS6G6, P. azotofixans, P. polymyxa strains such as ABP166 (deposited as NRRL B-50211)), Pandora, Pantoea (e.g., P. agglomerans strains such as NRRL B-21856, P. vagans strains such as C9-1), Paraglomus (e.g., P. brazilianum), Paraisaria, Pasteuria, Pasteuria (e.g., P. nishizawae strains such as Pn1, P. penefrans, P. ramose, P. sp. strains such as ATCC PTA-9643 and ATCC SD-5832, P. thornea, P. usage), Penicillium (e.g., P. albidum, P. aurantiogriseum, P. bilaiae (formerly known as P. bilaii and P. bilaji) strains such as ATCC 18309, ATCC 20851, ATCC 22348, NRRL 50162, NRRL 50169, NRRL 50776, NRRL 50777, NRRL 50778, NRRL 50777, NRRL 50778, NRRL 50779, NRRL 50780, NRRL 50781, NRRL 50782, NRRL 50783, NRRL 50784, NRRL 50785, NRRL 50786, NRRL 50787, NRRL 50788 and RS7B-SD1, P. brevicompactum strains such as AgRF18, P. canescens strains such as ATCC 10419, P. chyrsogenum, P. citreonigrum, P. cifrinum, P. digitatum, P. expansum strains such as ATCC 24692 and YT02, P. fellatanum strains such as ATCC 48694, P. frequentas, P. fuscum, P. fussiporus, P. gaestrivorus strains such as NRRL 50170, P. glabrum strains such as DAOM 239074 and CBS 229.28, P. glaucum, P. griseofulvum, P. implicatum, P. janthinellum strains such as ATCC 10455, P. lanosocoeruleum strains such as ATCC 48919, P. lilacinum, P. minioluteum, P. montanense, P. nigricans, P. oxalicum, P. pinetorum, P. pinophilum, P. purpurogenum, P. radicum strains such as ATCC 201836, FRR 4717, FRR 4719 and N93/47267, P. raistrickii strains such as ATCC 10490, P. rugulosum, P. simplicissimum, P. solitum, P. variabile, P. velutinum, P. viridicatum), Phingobacterium, Phlebiopsis (e.g., P. gigantea), Photorhabdus, Phyllobacterium (e.g., P. bourgognense, P. brassicacearum, P. catacumbae, P. endophyticum, P. ifriqiyense, P. leguminum, P. loti, P. myrsinacearum, P. sophorae, P. frifolii), Pichia (e.g., P. anomala strains such as WRL-076), Pisolithus (e.g., P. tinctorius), Planktothricoides, Plectonema, Pleurodesmospora, Pochonia (e.g., P. chlamydopora), Podonectria, Polycephalomyces, Prochlorocoous (e.g., P. marinus), Prochloron (e.g., P. didemni), Prochlorothrix, Pseudogibellula, Pseudomonas (e.g., P. agarici, P. antartica, P. aurantiaca, P. aureofaciens, P. azotifigens, P. azotoformans, P. balearica, P. blatchfordae, P. brassicacearum, P. brenneri, P. cannabina, P. cedrina, P. cepacia, P. chlororaphis strains such as MA 342, P. congelans, P. corrugata, P. costantinii, P. denifrificans, P. entomophila, P. fluorescens strains such as ATCC 27663, CL 145A and A506, P. fragii, P. fuscovaginae, P. fulva, P. gessardii, P. jessenii strains such as PS06, P. kilonensis, P. koreensis, P. libanensis, P. lili, P. lundensis, P. lutea, P. luteola, P. mandelii, P. marginalis, P. meditrranea, P. meridana, P. migulae, P. moraviensis, P. mucidolens, P. orientalis, P. oryzihabitans, P. palleroniana, P. panacis, P. parafulva, P. peli, P. pertucinogena, P. plecoglossicida, P. protogens, P. proteolytica, P. putida, P. pyrocina strains such as ATCC 15958, P. rhodesiae, P. sp. strains such as DSM 13134, P. striata, P. stutzeri, P. syringae, P. synxantha, P. taefrolens, P. thisvervalensis, P. tolaasii, P. veronii), Pseudozyma (e.g., P. flocculosa strains such as PF-A22 UL), Pythium (e.g., P. oligandrum strains such as DV 74), Rhizobium (e.g., R. aggregatum, R. alamii, R. alkalisoli, P. alvei, P. azibense, P. borbori, R. calliandrae, R. cauense, R. cellulosilyticum, R. daejeonense, R. endolithicum, R. endophyticum, R. etli, R. fabae, R. flavum, R. fredii, R. freirei, R. galegae, R. gallicum, R. giardinii, R. grahamii, R. hainanense, R. halophytocola, R. halotolerans, R. helanshanense, R. herbae, R. huautlense, R. indigoferae, R. jaguaris, R. kunmingense, R. laguerreae, R. larrymoorei, R. leguminosarum strains such as SO12A-2 (IDAC 080305-01), R. lemnae, R. leucaenae, R. loessense, R. lupini, R. lusitanum, R. mayense, R. mesoamericanum, R. mesosinicum, R. miluonense, R. mongolense, R. multihospitium, R. naphthalenivorans, R. nepotum, R. oryzae, R. pakistanensis, R. paknamense, R. paranaense, R. pefrolearium, R. phaseoli, R. phenanthrenilyticum, R. pisi, R. pongamiae, R. populi, R. pseudoryzae, R. pusense, R. qilianshanese, r. radiobacter, R. rhizogenes, R. rhizoryzae, R. rozettiformans, R. rubi, R. selenitireeducens, R. skierneiwicense, R. smilacinae, R. soli, R. sophorae, R. sophoriradicis, R. sphaerophysae, R. straminoryzae, R. sub baraonis, R. sullae, R. taibaishanense, R. tarimense, R. tibeticum, R. frifolii strains such as RP113-7, R. fropici strains such as SEMIA 4080, R. tubonense, R. undicola, R. vallis, R. viciae strains such as P1NP3Cst, SU303 and WSM 1455, R. vignae, R. vitis, R. yanglingense, R. yantingense), Rhizoctonia, Rhizopogon (e.g., R. amylopogon, R. fulvigleba, R. luteolus, R. villosuli), Rhodococcus, Saccharopolyspora (e.g., S. spinosa), Scleroderma (e.g., S. cepa S. cifrinum), Septobasidium, Serratia, Shinella (e.g., S. kummerowiae), Sinorhizoium (e.g., S. abri, S. adhaerens, S. americanum, S. arboris, S. chiapanecum, S. fredii strains such as CCBAU114 and USDA 205, S. garamanticus, S. indiaense, S. kostiense, S. kummerowiae, S.

medicae, S. meliloti strains such as MSDJ0848, S. mexicanus, S. numidicus, S. psoraleae, S. saheli, S. sesbaniae, S. sojae, S. terangae, S. xinjiangense), Sorosporella, Sphaerodes (e.g., S. mycoparasitica strains such as IDAC 301008-01), Spodoptera (e.g., S. littoralis), Sporodiniella, Steinernema (e.g., S. carpocapsae, S. feltiae, S. kraussei strains such as L137), Stenotrophomonas, Streptomyces (e.g., S. NRRL B-30145, S. M1064, S. WYE 53 (deposited as ATCC 55750), S. cacaoi strains such as ATCC 19093, S. galbus strains such as NRRL 30232, S. griseoviridis strains such as K61, S. lydicus strains such as WYEC 108 (deposited as ATCC 55445), S. violaceusniger strains such as YCED-9 (deposited as ATCC 55660)), Streptosporangium, Stillbella, Swaminathania, Talaromyces (e.g., T. aculeatus, T. flavus strains such as V117b), Tefranacrium, Thiobacillus, Tilachlidium, Tolypocladium, Tolypothrix, Torrubiella, Torulospora, Trenomyces, Trichoderma (e.g. T. asperellum strains such as SKT-1, T. atroviride strains such as LC52 and CNCM 1-1237, T. fertile strains such as JM41R, T. gamsii strains such as ICC 080, T. hamatum strains such as ATCC 52198, T. harzianum strains such as ATCC 52445, KRL-AG2, T-22, TH-35, T-39 and ICC012, T. polysporum, T. reesi strains such as ATCC 28217 T. sfromaticum, T. virens strains such as ATCC 58678, GL-3, GL-21 and G-41, T. viridae strains such as ATCC 52440, ICC080 and TV1), Typhula, Ulocladium (e.g., U. oudemansii strains such as HRU3), Uredinella, Variovorax, Verticillium (e.g., V. chlamydosporum, V. lecanii strains such as ATCC 46578), Vibrio, Xanthobacter, Xanthomonas. Xenorhabdus, Yersinia (e.g., Y. entomophaga strains such as O82KB8), Zoophthora That which is claimed:

1. A method of increasing plant yield, said method comprising:
    applying an inoculant composition comprising the *Penicillium bilaiae* strain having the *Penicillium bilaiae* strain having the deposit accession number NRRL 67154, the *Penicillium bilaiae* strain having the deposit accession number NRRL 67155, the *Penicillium bilaiae* strain having the deposit accession number NRRL 67156, the *Penicillium bilaiae* strain having the deposit accession number NRRL 67157, the *Penicillium bilaiae* strain having the deposit accession number NRRL 67158 and/or the *Penicillium bilaiae* strain having the deposit accession number NRRL 67159 to plant seed in an amount/concentration effective to increase the yield of plants grown from said seed, as compared to plants grown from untreated control seed.

2. The method of claim 1, wherein said inoculant composition comprises one or more hygroscopic polymers.

3. The method of claim 1, wherein said inoculant composition comprises one or more sugar alcohols.

4. The method of claim 1, wherein said inoculant composition comprises one or more sugar alcohols and one or more polyethylene glycols.

5. The method of claim 1, wherein said inoculant composition comprises at least $1 \times 10^4$ colony-forming units of the *Penicillium bilaiae* strain having the deposit accession number NRRL 67154, the *Penicillium bilaiae* strain having the deposit accession number NRRL 67155, the *Penicillium bilaiae* strain having the deposit accession number NRRL 67156, the *Penicillium bilaiae* strain having the deposit accession number NRRL 67157, the *Penicillium bilaiae* strain having the deposit accession number NRRL 67158 and/or the *Penicillium bilaiae* strain having the deposit accession number NRRL 67159 per gram and/or milliliter of said inoculant composition.

6. The method of claim 1, wherein said inoculant composition comprises one or more lipo-chitooligosaccharides.

7. The method of claim 1, wherein said inoculant composition comprises at least $1 \times 10^7$ colony-forming units of the *Penicillium bilaiae* strain having the deposit accession number NRRL 67154, the *Penicillium bilaiae* strain having the deposit accession number NRRL 67155, the *Penicillium bilaiae* strain having the deposit accession number NRRL 67156, the *Penicillium bilaiae* strain having the deposit accession number NRRL 67157, the *Penicillium bilaiae* strain having the deposit accession number NRRL 67158 and/or the *Penicillium bilaiae* strain having the deposit accession number NRRL 67159 per gram and/or milliliter of said inoculant composition.

8. The method of claim 1, wherein said inoculant composition is aqueous.

9. The method of claim 1, wherein said inoculant composition is non-aqueous.

10. A method of increasing plant yield, said method comprising:
    applying the isolated *Penicillium bilaiae* strain having the isolated *Penicillium bilaiae* strain having the deposit accession number NRRL 67154, the isolated *Penicillium bilaiae* strain having the deposit accession number NRRL 67155, the isolated *Penicillium bilaiae* strain having the deposit accession number NRRL 67156, the isolated *Penicillium bilaiae* strain having the deposit accession number NRRL 67157, the isolated *Penicillium bilaiae* strain having the deposit accession number NRRL 67158 and/or the isolated *Penicillium bilaiae* strain having the deposit accession number NRRL 67159 to plant seed in an amount/concentration effective to increase the yield of plants grown from said seed, as compared to plants grown from untreated control seed.

11. A method of increasing plant yield, said method comprising:
    introducing the isolated *Penicillium bilaiae* strain having the isolated *Penicillium bilaiae* strain having the deposit accession number NRRL 67154, the isolated *Penicillium bilaiae* strain having the deposit accession number NRRL 67155, the isolated *Penicillium bilaiae* strain having the deposit accession number NRRL 67156, the isolated *Penicillium bilaiae* strain having the deposit accession number NRRL 67157, the isolated *Penicillium bilaiae* strain having the deposit accession number NRRL 67158 and/or the isolated *Penicillium bilaiae* strain having the deposit accession number NRRL 67159 into a plant growth medium in an amount/concentration effective to increase the yield of plants grown in said plant growth medium, as compared to plants grown in an untreated control medium.

12. A method of increasing plant yield, said method comprising:
    introducing an inoculant composition comprising the *Penicillium bilaiae* strain having the *Penicillium bilaiae* strain having the deposit accession number NRRL 67154, the *Penicillium bilaiae* strain having the deposit accession number NRRL 67155, the *Penicillium bilaiae* strain having the deposit accession number NRRL 67156, the *Penicillium bilaiae* strain having the deposit accession number NRRL 67157, the *Penicillium bilaiae* strain having the deposit accession number NRRL 67158 and/or the *Penicillium bilaiae* strain having the deposit accession number NRRL 67159 into a plant growth medium in an amount/concentration effective to increase the yield of plants grown in said plant growth medium, as compared to plants grown in an untreated control medium.

13. The method of claim 12, wherein said inoculant composition comprises one or more hygroscopic polymers.

14. The method of claim 12, wherein said inoculant composition comprises one or more sugar alcohols.

15. The method of claim 12, wherein said inoculant composition comprises one or more sugar alcohols and one or more polyethylene glycols.

16. The method of claim 12, wherein said inoculant composition comprises at least $1 \times 10^4$ colony-forming units of the *Penicillium bilaiae* strain having the deposit accession number NRRL 67154, the *Penicillium bilaiae* strain having the deposit accession number NRRL 67155, the *Penicillium bilaiae* strain having the deposit accession number NRRL 67156, the *Penicillium bilaiae* strain having the deposit accession number NRRL 67157, the *Penicillium bilaiae* strain having the deposit accession number NRRL 67158 and/or the *Penicillium bilaiae* strain having the deposit accession number NRRL 67159 per gram and/or milliliter of said inoculant composition.

17. The method of claim 12, wherein said inoculant composition comprises one or more lipo-chitooligosaccharides.

18. The method of claim 12, wherein said inoculant composition comprises at least $1 \times 10^7$ colony-forming units of the *Penicillium bilaiae* strain having the deposit accession number NRRL 67154, the *Penicillium bilaiae* strain having the deposit accession number NRRL 67155, the *Penicillium bilaiae* strain having the deposit accession number NRRL 67156, the *Penicillium bilaiae* strain having the deposit accession number NRRL 67157, the *Penicillium bilaiae* strain having the deposit accession number NRRL 67158 and/or the *Penicillium bilaiae* strain having the deposit accession number NRRL 67159 per gram and/or milliliter of said inoculant composition.

19. The method of claim 12, wherein said inoculant composition is aqueous.

20. The method of claim 12, wherein said inoculant composition is non-aqueous.

* * * * *